United States Patent
Luesch et al.

(10) Patent No.: US 9,730,970 B2
(45) Date of Patent: Aug. 15, 2017

(54) SEAWEED EXTRACTS, UNSATURATED ALDEHYDES, AND METHODS OF TREATMENT

(71) Applicants: University of Florida Research Foundation, Inc., Gainesville, FL (US); Smithsonian Institution, Washington, DC (US)

(72) Inventors: Hendrik Luesch, Gainesville, FL (US); Valerie J. Paul, Fort Pierce, FL (US); Ranjala Ratnayake, Gainesville, FL (US)

(73) Assignees: University of Florida Research Foundation, Inc., Gainesville, FL (US); Smithsonian Institution, Washington, DC (US)

( * ) Notice: Subject to any disclaimer, the term of this patent is extended or adjusted under 35 U.S.C. 154(b) by 52 days.

(21) Appl. No.: 14/846,544

(22) PCT Filed: Mar. 14, 2014

(86) PCT No.: PCT/US2014/029314
§ 371 (c)(1),
(2) Date: Sep. 4, 2015

(87) PCT Pub. No.: WO2014/144765
PCT Pub. Date: Sep. 18, 2014

(65) Prior Publication Data
US 2016/0051604 A1    Feb. 25, 2016

Related U.S. Application Data

(60) Provisional application No. 61/790,308, filed on Mar. 15, 2013, provisional application No. 61/861,795, filed on Aug. 2, 2013.

(51) Int. Cl.
| | |
|---|---|
| *A01N 65/00* | (2009.01) |
| *A61K 36/05* | (2006.01) |
| *A61K 31/11* | (2006.01) |
| *A61K 36/02* | (2006.01) |

(52) U.S. Cl.
CPC .............. *A61K 36/05* (2013.01); *A61K 31/11* (2013.01); *A61K 36/02* (2013.01); *A61K 2236/33* (2013.01)

(58) Field of Classification Search
CPC ...................................................... A61K 36/00
USPC ....................................................... 424/725
See application file for complete search history.

(56) References Cited

PUBLICATIONS

Wang, R., et al., "Seaweed extracts and unsaturated fatty acid constituents from the green alga *Ulva lactuca* as activators of the cytoprotective Nrf2-ARE pathway", Free Radical Biology and Medicine, Jan. 4, 2013; pp. 141-153.
Vijayavel, K., et al., "In vitro antioxidant and antimicrobial activities of two Hawaiian marine Limu: Ulva fasciata (Chlorophyta) and Gracilaria salicornia (Rhodophyta)", Journal of Medicinal Food, 2010; pp. 41494-1499.
Kajiwara, T., et al., "Antimicrobial browning-inhibitory effect of flavor compounds in seaweeds", Journal of Applied Phycology, 2006, pp. 413-422.
Ryu, M. J., et al., "The green algae *Ulva fasciata* Delile extract induces apoptotic cell death in human colon cancer cells", In Vitro Cellular & Developmental Biology-Animal, Jan. 9, 2013, pp. 74-81.
Jeong, W. S., et al., "Nrf2: a potential molecular target for cancer chemoprevention by natural compounds", Antioxidants & Redox Signaling, 2006, pp. 99-106.
Ratnayake, R., et al., "Cultivated sea lettuce is a multiorgan protector from oxidative and inflammatory stress by enhancing the endogenous antioxidant defense system", Cancer Prevention Research, Sep. 2013, pp. 989-999.
International Search Report for PCT/US2014/029314 dated Aug. 7, 2014.

*Primary Examiner* — Michael Meller
(74) *Attorney, Agent, or Firm* — Wolf, Greenfield & Sacks, P.C.

(57) ABSTRACT

The instant invention relates to seaweed extract compositions, processes for isolation, isolated active agents, and methods of treating disease, disorders and conditions in a subject, including, reactive oxygen species (ROS)-mediated diseases and diseases mediated through the activation of the Nrf2-ARE (antioxidant response element) pathway, including proliferative diseases and disorders, Alzheimer's disease, stroke, and certain diseases and disorders of aging and associated with aging and exposure, by use of the extracts, compounds, and compositions thereof.

1 Claim, 18 Drawing Sheets

FIG. 1A  Extraction and fractionation of cultivated *Ulva* sp. and assessment of ARE-related transcriptional effects in neuroblastoma and prostate cancer cells.
(A) Cultivated *Ulva* was extracted successively with EtOAc and EtOH and extracts were subjected to chromatography. Fractions indicated in bold showed greatest ARE activity and were used for more detailed studies.
(B–D) Dose-dependent ARE activities (normalized to vehicle control) of prioritized fractions in IMR-32 neuroblastoma cells. *Tert*-butylhydroquinone (tBHQ, 10 μM) served as a positive control.
(C,D) Effects on endogenous *NQO1* (C) and *NRF2* (D) transcript levels as measured by RT-qPCR.
(E–G) Dose-dependent ARE activities (normalized to vehicle control) of prioritized fractions in LNCaP prostate cancer cells as carried out for IMR-32 cells (panels B–D, respectively). Sulforaphane (SF, 10 μM) served as a positive control.

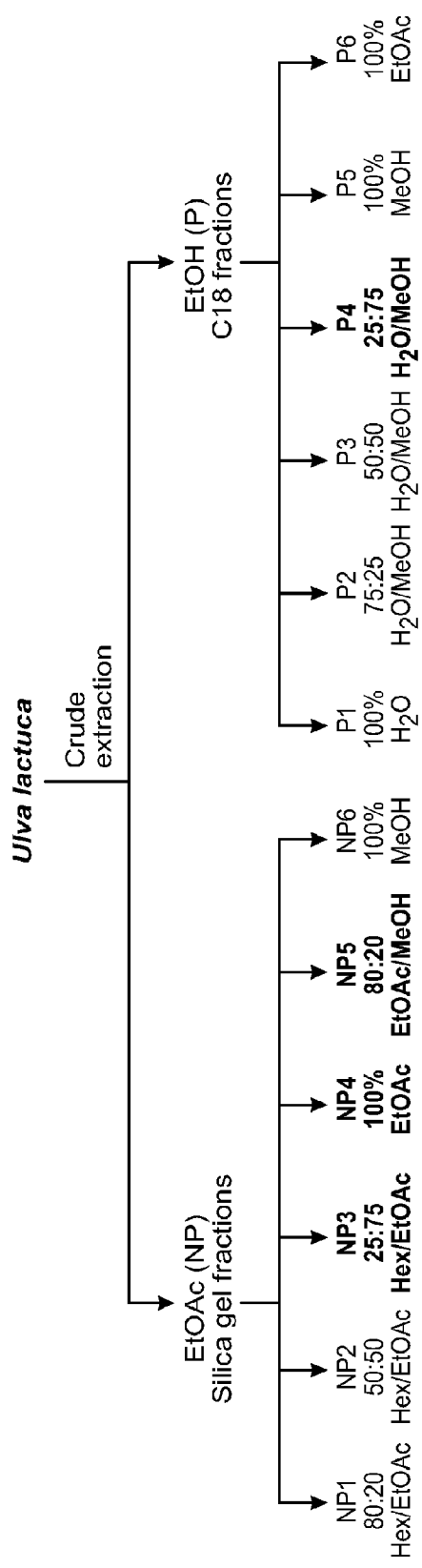

$^1$H NMR of 8-chloro-6,7-dihydroxy-deca-2,4-dienal (4) in $d_4$-MeOH.

COSY spectrum of 8-chloro-6,7-dihydroxy-deca-2,4-dienal (4) in $d_4$-MeOH.

TOCSY spectrum of 8-chloro-6,7-dihydroxy-deca-2,4-dienal (4) in $d_4$-MeOH.

NOESY spectrum of 8-chloro-6,7-dihydroxy-deca-2,4-dienal (4) in $d_4$-MeOH.

HSQC spectrum of 8-chloro-6,7-dihydroxy-deca-2,4-dienal (4) in $d_4$-MeOH.

HMBC spectrum of 8-chloro-6,7-dihydroxy-deca-2,4-dienal (4) in $d_4$-MeOH.

FIG. 9A

Downstream responses and mechanism of ARE-controlled gene expression of active fractions in IMR-32 cells.
(A) Effect on NQO1 protein levels. Asterisks (*) indicate toxic concentrations.
(B) Analysis of Nrf2 nuclear translocation and stabilization by Western blot analysis using previously established active fraction concentrations.
(C) Cells were transfected with siRNAs targeting NRF2 or with non-targeting control siRNAs (50 nM).
(D) Effect of pharmacological kinase inhibitors on natural products-induced NQO1 protein expression.
(E) Time-dependent effects on glutathione levels. Results are represented as means ± SD (n = 3).

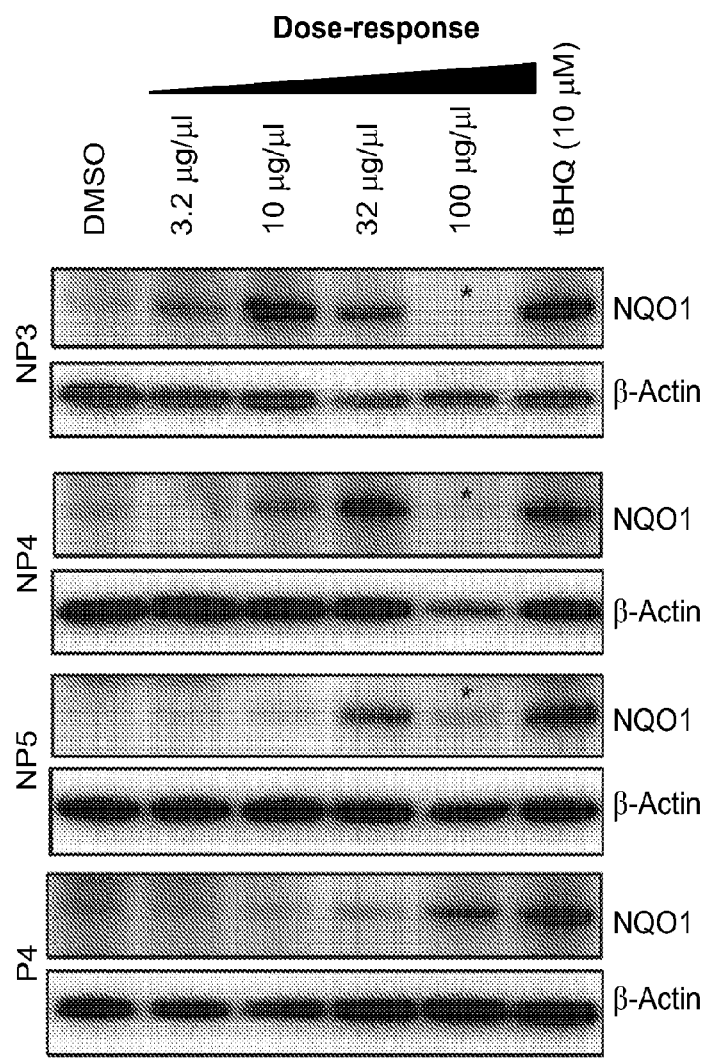

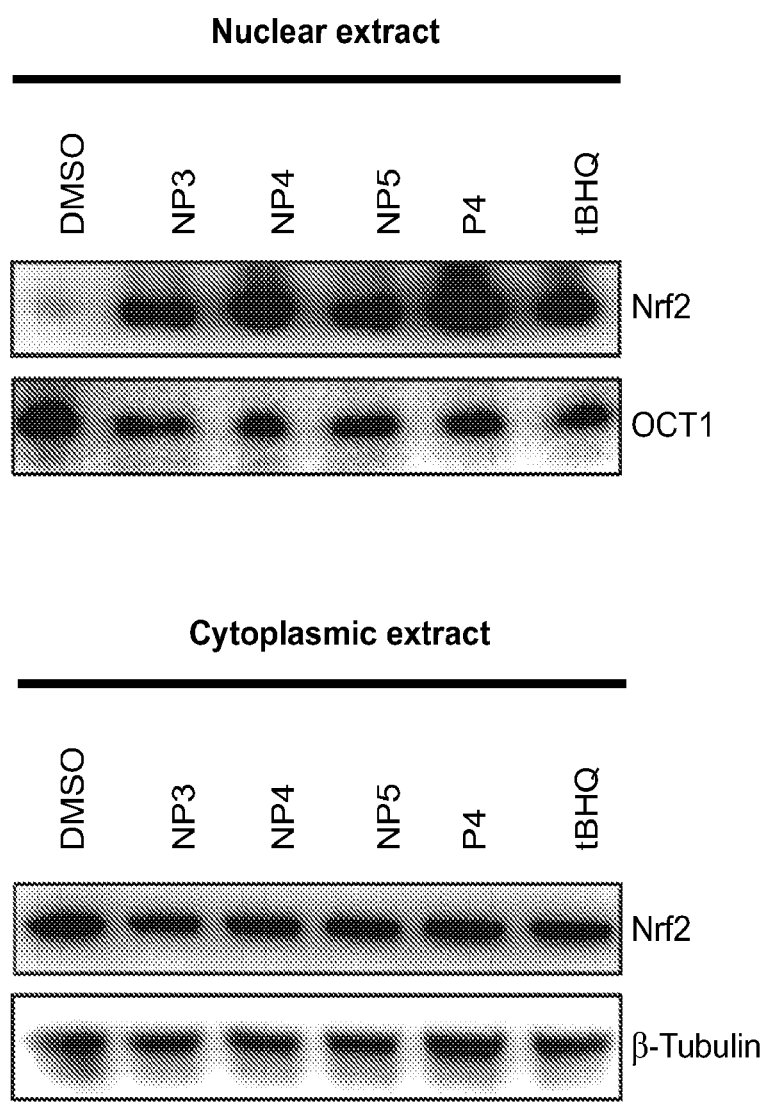

FIG. 10

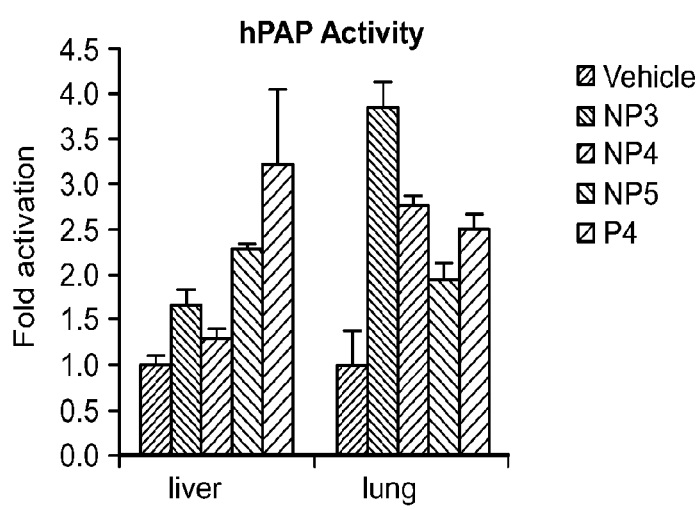

| Fractions | Tissue-dependent *Nqo1* induction (fold) | | | | |
|---|---|---|---|---|---|
| | Stomach | Small intestines | Colon | Liver | Lung |
| NP3 | 82 ± 22 | 1.3 ± 0.1 | 3.3 ± 0.1 | 11.0 ± 2.0 | 2.3 ± 0.4 |
| NP4 | 237 ± 38 | 1.6 ± 0.5 | 3.4 ± 2.0 | 21.4 ± 6.0 | 1.8 ± 0.3 |
| NP5 | 36 ± 14 | 3.9 ± 1.0 | 3.8 ± 2.0 | 10.8 ± 3.0 | 2.1 ± 0.3 |
| P4 | 14.7 ± 9.0 | 11.0 ± 0.1 | 6.2 ± 4.0 | 2.7 ± 0.3 | 2.0 ± 0.9 |

>50-fold   >20-fold   >10-fold   >5-fold   >2-fold   <2-fold

Activation of ARE reporter and induction of endogenous Nqo1 transcript levels in vivo 12 h after gavage-feeding of Ulva extract mixtures.
(A) Lung and liver tissues were analyzed for hPAP activity.
(B) Relative Nqo1 transcript changes and heatmap to visualize trends in fraction-dependent Nqo1 induction for various tissues. For each mouse, tissue samples were analyzed in triplicate. Results are represented as fold induction ± SEM.

FIG. 11
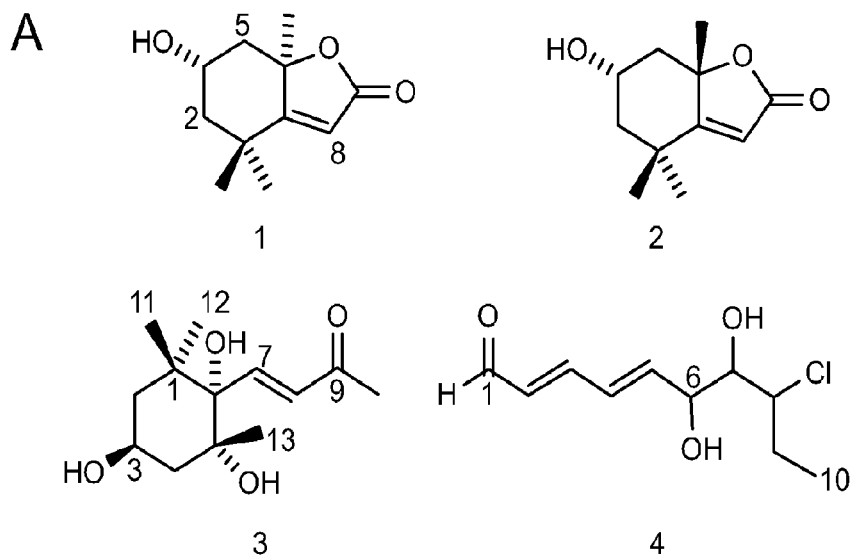
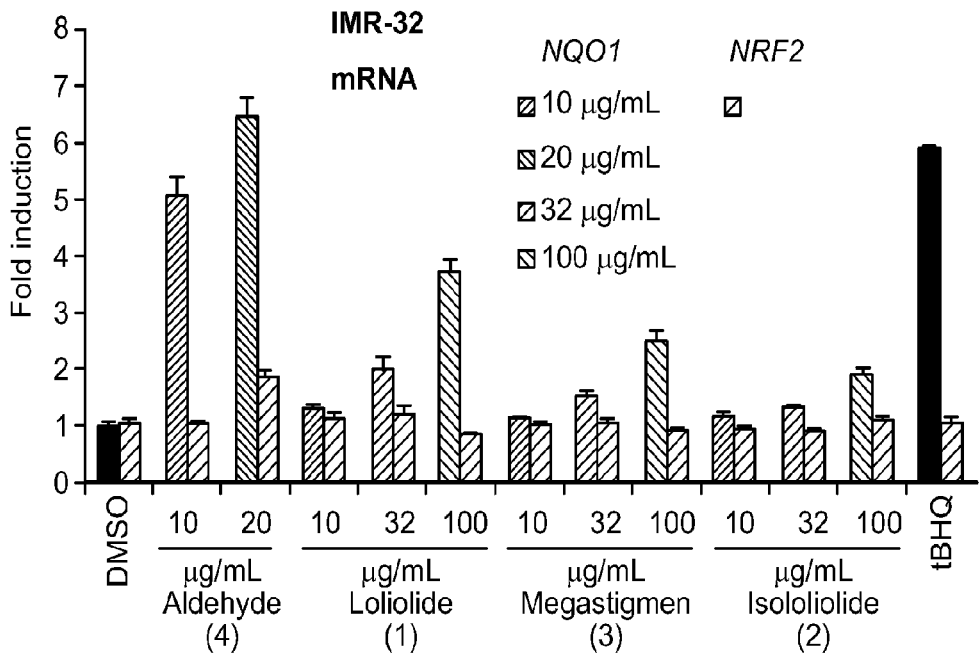
Chemical analysis and biological characterization of purified active components. (B) Effects of purified compounds on NQO1 and NRF2 transcript levels in IMR-32 cells as measured by RT-qPCR. GAPDH expression was used as internal control for normalization.

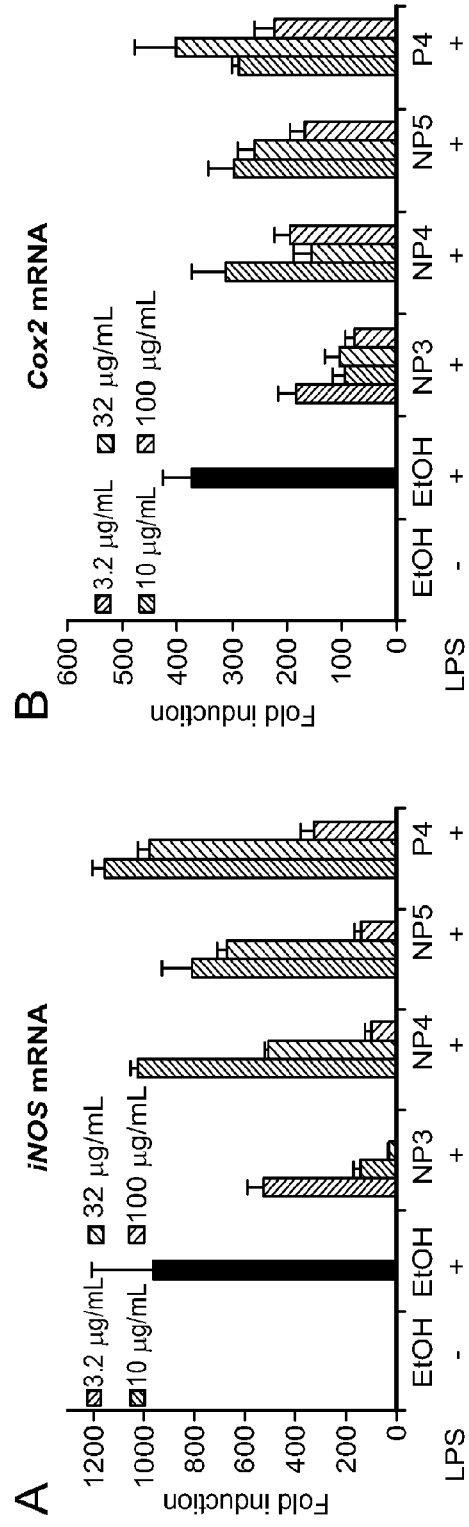

FIG. 12

Effects of prioritized fractions on pro-inflammatory gene expression and mediators in macrophage RAW 264.7 cells and mouse embryonic fibroblasts (MEFs): iNOS mRNA (A), Cox2 mRNA (B), NO levels (C), PGE2 levels (D), Nqo1 mRNA (E), NO levels after IFN-γ stimulus (F), Measurement of Nqo1 activity in wild-type, Nrf2-/- and Keap1-/- MEFs (G), Measurement of NO levels in wild-type and Nrf2-/- MEFs after IFN-γ (10 ng/mL) and TNF-α stimulation (H).

SEAWEED EXTRACTS, UNSATURATED ALDEHYDES, AND METHODS OF TREATMENT

CROSS-REFERENCE TO RELATED APPLICATIONS

This application is a U.S. National Phase under 35 U.S.C. §371 of PCT International Application No. PCT/US2014/029314, filed Mar. 14, 2014, which claims the benefit of U.S. Provisional Patent Application No. 61/790,308, filed Mar. 15, 2013, and Provisional Application No. 61/861,795, filed Aug. 2, 2013, the entire contents of the aforementioned applications are hereby incorporated herein by reference.

STATEMENT OF RIGHTS TO INVENTIONS MADE UNDER FEDERALLY SPONSORED RESEARCH

The invention was made with government support under Grant No. CA133681 awarded by the National Institutes of Health. The government has certain rights in the invention.

BACKGROUND

This invention relates to seaweed extract compositions, enriched active fractions, isolated active agents, and methods of use for the treatment and/or prevention of reactive oxygen species (ROS)-mediated diseases and diseases alleviated or prevented through the activation of the Nrf2-ARE (antioxidant response element) pathway, such as inflammation, cancer, Alzheimer's disease and other neurodegenerative disorders, stroke, chronic kidney disease, type II diabetes, and aging itself.

In aerobes, reactive oxygen species (ROS) is produced during cellular respiration and energy metabolism [Halliwell, B. Biochemistry of oxidative stress. *Biochem Soc Trans.* 35:1147-50; 2007]. In a healthy cell, the level of ROS is tightly regulated by the antioxidant defense system. However, upon environmental stress or cellular damage, the cell cannot readily detoxify the ROS generated and may thereby suffer from oxidative stress, which is implicated in the pathogenesis of many age-related diseases, such as inflammation, cancer, Alzheimer's disease and other neurodegenerative disorders, stroke, chronic kidney disease, type II diabetes, and aging itself [Liu, Y.; Kern, J. T.; Walker, J. R.; Johnson, J. A.; Schultz, P. G.; Luesch, H. A genomic screen for activators of the antioxidant response element. *Proc Natl Acad Sci USA.* 104:5205-10; 2007; Dinkova-Kostova A T, Massiah M A, Bozak R E, Hicks R J, Talalay P. Potency of Michael reaction acceptors as inducers of enzymes that protect against carcinogenesis depends on their reactivity with sulfhydryl groups. Proc Natl Acad Sci USA 2001; 98:3404-3409; Ramos-Gomez M, Kwak M-K, Dolan P M, Itoh K, Yamamoto M, Talalay P et. al. Sensitivity to carcinogenesis is increased and chemoprotective efficacy of enzyme inducers is lost in nrf2 transcription factor-deficient mice. Proc Natl Acad Sci USA 2001; 98:3410-3415; van Muiswinkel F L, Kuiperij H B. The Nrf2-ARE signaling pathway: promising drug target to combat oxidative stress in neurodegenerative disorders. Curr Drug Targets CNS Neurol Disord 2005; 4:267-281; Dinkova-Kostova, A T, Liby K T, Stephenson K K, Holtzclaw W D, Gao X, Suh N et. al. Extremely potent triterpenoid inducers of the phase 2 response: Correlations of protection against oxidant and inflammatory stress. Proc Natl Acad Sci USA 2005; 102: 4584-4589; Chen X-L, Kunsch C. Induction of cytoprotective genes through Nrf2/antioxidant response element pathway: a new therapeutic approach for the treatment of inflammatory diseases. Curr Pharm Des 2004; 10:879-891; Pergola P E, Raskin P, Toto R D, Meyer C J, Huff J W, Grossman E B et. al. BEAM Study Investigators. Bardoxolone methyl and kidney function in CKD with type 2 diabetes. N Engl J Med 2011; 365:327-336].

While antioxidant activity is commonly associated with direct radical scavenging activity, an alternative way to increase the antioxidant status of a cell or body is to concertedly enhance the endogenous defense system consisting of antioxidant enzymes and detoxification enzymes, which presumably causes a more sustained, longer-lasting effect. Phase II and other antioxidant enzymes are commonly regulated by the antioxidant response element (ARE) on the transcriptional level [Kensler T W, Wakabayashi N, Biswal S. Cell survival responses to environmental stresses via the Keap1-Nrf2-ARE pathway. *Annu. Rev. Pharmacol. Toxicol.* 47:89-116; 2007]. Increased expression of these enzymes correlates with a decrease in cellular damage by radical oxygen species (ROS), which are implicated in inflammation and the pathogenesis of many age-related disorders, including cancer, neurodegeneration, and aging itself [Chen X-L, Kunsch C. Induction of cytoprotective genes through Nrf2/antioxidant response element pathway: a new therapeutic approach for the treatment of inflammatory diseases. *Curr. Pharm. Des.* 10:879-891; 2004; Surh Y J. Cancer chemoprevention with dietary phytochemicals. *Nat. Rev. Cancer* 3:768-780; 2003; van Muiswinkel F L, Kuiperij H B. The Nrf2-ARE signaling pathway: promising drug target to combat oxidative stress in neurodegenerative disorders. *Curr. Drug Targets CNS Neurol. Disord.* 4:267-281; 2005]. In humans, the antioxidant response element (ARE) regulates the expression of cytoprotective antioxidant enzymes [e.g., heme oxygenase-1 (HO-1), glutathione-S-transferases (GSTs), NAD(P)H:quinone oxidoreductase 1 (NQO1)], which contribute to the endogenous defense against oxidative stress [Kensler T W, Wakabayashi N, Biswal S. Cell survival responses to environmental stresses via the Keap1-Nrf2-ARE pathway. *Annu. Rev. Pharmacol. Toxicol.* 47:89-116; 2007]. The major transcription factor involved in the induction of phase II enzymes is nuclear factor E2-related factor 2 (Nrf2), a Cap 'n' Collar (CNC) type basic region-leucine zipper (bZip) transcription factor that, upon activation by ARE inducers, translocates to the nucleus, binds to the ARE sequence as a heterodimer with one of the small bZip proteins, Mafs, and activates ARE-dependent genes. Nrf2 is negatively regulated by the cysteine-rich protein Keap1. Keap1 serves to sequester Nrf2 in the cytoplasm and interacts with Cul3-based E3 ubiquitin ligase to target Nrf2 for proteasomal degradation [Dinkova-Kostova A T, Holtzclaw W D, Kensler T W. The role of Keap1 in cellular protective responses. *Chem. Res. Toxicol.* 18:1779-1791; 2005; Kobayashi M, Yamamoto M. Nrf2-Keap1 regulation of cellular defense mechanisms against electrophiles and reactive oxygen species. *Adv. Enzyme Regul.* 46:113-140; 2006; Zhang D D. Mechanistic studies of the Nrf2-Keap1 signaling pathway. *Drug. Metab. Rev.* 38:769-789; 2006].

Nrf2 knockout mice show diminished detoxification capabilities, decreased responsiveness to chemoprotective agents, and enhanced susceptibility to oxidative stress induced cell death [Chan K, Han X-D, Kan Y W. An important function of Nrf2 in combating oxidative stress: detoxification of acetaminophen. *Proc. Natl. Acad. Sci. USA* 98:4611-4616; 2001; Ramos-Gomez M, Kwak M-K, Dolan P M, Itoh K, Yamamoto M, Talalay P, et al. Sensitivity to carcinogenesis is increased and chemoprotective efficacy of enzyme inducers is lost in nrf2 transcription factor-deficient mice. *Proc. Natl. Acad. Sci. USA* 98:3410-3415; 2001; Calkins M J, Jakel R J, Johnson D A, Chan K, Kan Y W, Johnson J A. Protection from mitochondrial complex II inhibition in vitro and in vivo by Nrf2-mediated transcription. *Proc. Natl. Acad. Sci. USA* 102:244-249; 2005]. Conversely, Nrf2 overexpression protects from oxidative stress [Chan K, Kan Y W, Johnson J A. Protection from mitochondrial complex II inhibition in vitro and in vivo by Nrf2-mediated transcription. *Proc. Natl. Acad. Sci. USA* 102:244-249; 2005]. NQO1-deficient individuals are at a considerably higher risk of developing leukemia following occupational exposure to benzene [Nebert D W, Roe A L, Vandale S E, Bingham E, Oakley G G. NAD(P)H:quinone oxidoreductase (NQO1) polymorphism, exposure to benzene, and predisposition to disease: a HuGE review. *Genet. Med.* 4:62-70; 2002]. The activation of the Nrf2-ARE pathway is a valid cancer preventive strategy, and sulforaphane, a constituent of broccoli, is an example of a cancer preventive natural product that acts through this mechanism [Surh Y J. Cancer chemoprevention with dietary phytochemicals. *Nat. Rev. Cancer* 3:768-780]. We hypothesized and preliminarily demonstrated that some seaweeds are able to activate this signaling pathway and that some of the beneficial, particularly antioxidant, properties may be mediated through ARE activation as opposed to only direct scavenging properties [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013].

ARE activation may also be particularly relevant to prostate cancer [Sikka S C. Role of oxidative stress response elements and antioxidants in prostate cancer pathobiology and chemoprevention—a mechanistic approach. *Curr. Med. Chem.* 10:2679-2692; 2003]. The most common hallmark in prostate cancer is the silencing of glutathione-S-transferase (GST)-π (GSTP1) due to DNA methylation, which is nearly universal [Lee W H, Morton R A, Epstein J I, Brooks J D, Campbell P A, Bova G S, et al. Cytidine methylation of regulatory sequences near the π-class glutathione S-transferase gene accompanies human prostatic carcinogenesis. *Proc. Natl. Acad. Sci. USA* 91:11733-11737; 1994; Lee W-H, Isaacs W B, Bova G S, Nelson W G. CG island methylation changes near the GSTP1 gene in prostatic carcinoma cells detected using the polymerase chain reaction: a new prostatic biomarker. *Cancer Epidemiol. Biomark. Prev.* 6:443-450; 1997; Lin X, Tascilar M, Lee W H, Vies W J, Lee B H, Veeraswamy R, et al. GSTP1 cpG island hypermethylation is responsible for the absence of GSTP1 expression in human prostate cancer cells. *Am. J. Pathol.* 159:1815-1826; 2001]. Because of the lack of GSTP1 expression in prostate cancer (regardless of grade or stage), induction of GSTs and other phase II enzymes through ARE activation is a promising prostate cancer-preventive strategy [Lee W H, Morton R A, Epstein J I, Brooks J D, Campbell P A, Bova G S, et al. Cytidine methylation of regulatory sequences near the π-class glutathione S-transferase gene accompanies human prostatic carcinogenesis. *Proc. Natl. Acad. Sci. USA* 91:11733-11737; 1994; Lee W-H, Isaacs W B, Bova G S, Nelson W G. CG island methylation changes near the GSTP1 gene in prostatic carcinoma cells detected using the polymerase chain reaction: a new prostatic biomarker. *Cancer Epidemiol. Biomark Prev.* 6:443-450; 1997; Lin X, Tascilar M, Lee W H, Vies W J, Lee B H, Veeraswamy R, et al. GSTP1 cpG island hypermethylation is responsible for the absence of GSTP1 expression in human prostate cancer cells. *Am. J. Pathol.* 159:1815-1826; 2001; Brooks J D, Paton V G, Vidanes G. Potent induction of phase 2 enzymes in human prostate cells by sulforaphane. *Cancer Epidemiol. Biomark. Prev.* 10:949-954; 2001; Brooks J D, Goldberg M F, Nelson L A, Wu D, Nelson W G. Identification of potential prostate cancer preventive agents through induction of quinone reductase in vitro. *Cancer Epidemiol. Biomark. Prev.* 11:868-875; 2002]. While prostate cancer is the second leading cause of cancer death in American men, prostate cancer is rarely diagnosed and contributes little to cancer mortality in Asia [Greenlee R T, Hill-Harmon M B, Murray T, Thun M. Cancer statistics, 2001. *CA Cancer J. Clin.* 51:15-36; 2001; Carter B S, Carter H B, Isaacs J T. Epidemiologic evidence regarding predisposing factors to prostate cancer. *Prostate* 16:187-197; 1990; Yu H, Harris R E, Gao Y T, Gao R, Wynder E L. Comparative epidemiology of cancers of the colon, rectum, prostate, and breast in Shanghai, China versus the United States. *Int. J. Epidemiol.* 20:76-81; 1991]. However, men migrating from Asia to the USA increase their risk, which remains elevated in their male descendents [Shimizu H, Ross R K, Bernstein L, Yatani R, Henderson B E, Mack T M. Cancers of the prostate and breast among Japanese and white immigrants in Los Angeles County. *Br. J. Cancer* 63:963-966; 1991; Whittemore A S, Kolonel L N, Wu A H, John E M, Gallagher R P, Howe G R, et al. Prostate cancer in relation to diet, physical activity, and body size in blacks, whites, and Asians in the United States and Canada. *J. Natl. Cancer Inst.* 87:652-661; 1995; Haenzel W, Kurihara M, Mortality from cancer and other diseases among Japanese men in the United States. *J. Natl. Cancer Inst.* 40:43-68; 1968; Danley K L, Richardson J L, Bernstein L, Langholz B, Ross R K. Prostate cancer: trends in mortality and stage-specific incidence rates by racial/ethnic group in Los Angeles County, California (United States). *Cancer Cause Control* 6:492-498; 1995]. While environmental factors may play a role, this observation may be attributable to lifestyle changes. Notably, diet in Asia largely includes seaweed, suggesting a possible connection between algae consumption and decreased prostate cancer risk. Many other diseases, including those with an inflammation component, are caused by aberrant oxidative stress and may be prevented or interfered with via enhancing the cellular antioxidant status.

Marine algae (seaweeds) have been used as a food source and medicine for centuries [Chapman V J, Chapman D J. *In Seaweeds and Their Uses*. (Chapman and Hall, New York) pp 62-67; 1980]. This includes green algae (Chlorophyta), red algae (Rhodophyta) and brown algae (Ochrophyta). Consumption of seaweed, which predominantly occurs in Japan, was found to be inversely related to various cancers, including colon, rectal and stomach cancer [Hoshiyama Y, Sekine T, Sasaba T. A case-control study of colorectal-cancer and its relation to diet, cigarettes, and alcohol-consumption in Saitama Prefecture, Japan. *Tohoku J. Exp. Med.* 171:153-165; 1993; Hoshiyama Y, Sasaba T. A case-control study of single and multiple stomach cancers in Saitama Prefecture, Japan. *Jpn. J. Cancer Res.* 83:937-943; 1992]. Seaweed is a major part of the Okinawan food culture, and Okinawans have the longest life expectancy in the world and low disability rates [Sho H. History and characteristics of Okinawan longevity food. *Asia Pac. J. Clin. Nutr.* 10:159-164; 2001]. Numerous beneficial properties of algal extracts and constituents have been reported, however, usually only in a descriptive manner, without pinpointing specific bioactive components or invoking specific molecular pathways. Green algae of the genus *Ulva*, also known as sea lettuce, are among the most commonly consumed seaweeds. They reportedly have anti-inflammatory and antitumoral properties and are implicated in cancer prevention and detoxification. For example, crude extracts of *U. reticulata* given to rats attenuated acetaminophen-induced hepatotoxicity by improving the hepatic antioxidant status [Balaji Raghavendra Rao H, Sathivel A, Devaki T. Antihepatotoxic nature of *Ulva reticulata* (Chlorophycaeae) on acetaminophen-induced hepatotoxicity in experimental rats. *J. Med. Food* 7:495-497; 2004]. It has been postulated that *Ulva* extract protects the membrane from damage by toxic reactive metabolites produced by acetaminophen biotransformation [Balaji Raghavendra Rao H, Sathivel A, Devaki T. Antihepatotoxic nature of *Ulva reticulata* (Chlorophycaeae) on acetaminophen-induced hepatotoxicity in experimental rats. *J. Med. Food* 7:495-497; 2004*]*. *U. conglobata* has been found to have neuroprotective and anti-inflammatory activity, while *U. lactuca* has antitumor and immunostimulating effects [Jin D-Q, Lim C S, Sung J-Y, Choi H G, Ha I, Han J-S. *Ulva conglobata*, a marine algae, has neuroprotective and anti-inflammatory effects in murine hippocampal and microglial cells. *Neurosci. Lett.* 402:154-158; 2006; Lee D G, Hyun J W, Kang K A, Lee J O, Lee S H, Ha B J, et al. *Ulva lactuca*: a potential seaweed for tumor treatment and immune stimulation. *Biotechnol. and Bioprocess E* 9:236-238; 2004]. The antioxidant activity of *U. pertusa* has been attributed to polysaccharides with high sulfate content [Qi H, Zhang Q, Zhao T, Chen R, Zhang H, Niu X, et al. Antioxidant activity of different sulfate content derivatives of polysaccharide extracted from *Ulva pertusa* (Chlorophyta) in vitro. *Int. J. Biol. Macromol.* 37:195-199; 2005]. We recently described that *U. lactuca* can increase the cellular antioxidant status through an alternative mechanism, and attributed this activity in part to the presence of monounsaturated fatty acid constituents [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013].

Many naturally occurring small molecule inducers of the Nrf2-ARE pathway have been identified and explored as chemopreventive or therapeutic agents. For example, curcumin [Balogun, E.; Hogue, M.; Gong, P.; Killeen, E.; Green, C. J.; Foresti, R.; Alam, J.; Motterlini, R. Curcumin activates the haem oxygenase-1 gene via regulation of Nrf2 and the antioxidant-responsive element. *Biochem J.* 371: 887-95; 2003], the active ingredient in traditional herbal remedy and dietary spice turmeric (*Curcuma longa*) is currently in clinical trials for multiple conditions, including several cancers and Alzheimer's disease [Hatcher, H.; Planalp, R.; Cho, J.; Torti, F. M.; Torti, S. V. Curcumin: from ancient medicine to current clinical trials. *Cell Mol Life Sci.* 65:1631-52; 2008]. The skin of red grapes (*Vitis vinifera*) is rich in resveratrol [Langcake, P.; Pryce, R. J. Production of Resveratrol by *Vitis-Vinifera* and Other Members of Vitaceae as a Response to Infection or Injury. *Physiological Plant Pathology*. 9:77-86; 1976; Rubiolo, J. A.; Mithieux, G.; Vega, F. V. Resveratrol protects primary rat hepatocytes against oxidative stress damage: activation of the Nrf2 transcription factor and augmented activities of antioxidant enzymes. *Eur J Pharmacol*. 591:66-72; 2008], which was found to be responsible for an inverse relationship between grape consumption and breast cancer occurrence in an epidemiologic study [Levi, F.; Pasche, C.; Lucchini, F.; Ghidoni, R.; Ferraroni, M.; La Vecchia, C. Resveratrol and breast cancer risk. *Eur J Cancer Prev.* 14:139-42; 2005]. In a clinical setting, resveratrol was observed to induce the re-expression of tumor suppressor genes in a group of women who are at increased risk of breast cancer [Zhu, W.; Qin, W.; Zhang, K.; Rottinghaus, G. E.; Chen, Y. C.; Kliethermes, B.; Sauter, E. R. Trans-resveratrol alters mammary promoter hypermethylation in women at increased risk for breast cancer. *Nutr Cancer.* 64:393-400; 2012]. The detoxification enzyme inducer, sulforaphane [Kensler, T. W.; Egner, P. A.; Agyeman, A. S.; Visvanathan, K.; Groopman, J. D.; Chen, J. G.; Chen, T. Y.; Fahey, J. W.; Talalay, P. Keap1-Nrf2 Signaling: A Target for Cancer Prevention by Sulforaphane. *Top Curr Chem.* 2012], was found in many cruciferous vegetables. It has been shown that a daily regimen of hot water infused with 3-day-old broccoli sprouts has promising results in cancer chemoprevention in healthy individuals [Kensler, T. W.; Chen, J. G.; Egner, P. A.; Fahey, J. W.; Jacobson, L. P.; Stephenson, K. K.; Ye, L.; Coady, J. L.; Wang, J. B.; Wu, Y.; Sun, Y.; Zhang, Q. N.; Zhang, B. C.; Zhu, Y. R.; Qian, G. S.; Carmella, S. G.; Hecht, S. S.; Benning, L.; Gange, S. J.; Groopman, J. D.; Talalay, P. Effects of glucosinolate-rich broccoli sprouts on urinary levels of aflatoxin-DNA adducts and phenanthrene tetraols in a randomized clinical trial in He Zuo township, Qidong, People's Republic of China. *Cancer Epidemiol Biomarkers Prev.* 14:2605-13; 2005]. Broccoli sprouts (*Brassica oleracea italica*) contain high levels of its precursor, glucoraphanin [Farnham, M. W.; Stephenson, K. K.; Fahey, J. W. Glucoraphanin level in broccoli seed is largely determined by genotype. *Hortscience.* 40:50-53; 2005], which can be enzymatically converted to sulforaphane in the gastrointestinal tract after ingestion [Zhang, Y.; Talalay, P.; Cho, C. G.; Posner, G. H. A major inducer of anticarcinogenic protective enzymes from broccoli: isolation and elucidation of structure. *Proc Natl Acad Sci USA.* 89:2399-403; 1992].

The marine environment has also proven to be a rich source of potent compounds with diverse therapeutic properties [Newman, D. J.; Cragg, G. M. Marine natural products and related compounds in clinical and advanced preclinical trials. *J Nat Prod.* 67:1216-38; 2004; Montaser, R.; Luesch, H. Marine natural products: a new wave of drugs? *Future Med Chem.* 3:1475-89; 2011]. For example, several molecules with anti-cancer activities based on leads from marine cyanobacteria have been described [Taori, K.; Paul, V. J.; Luesch, H. Structure and activity of largazole, a potent antiproliferative agent from the Floridian marine cyanobacterium *Symploca* sp. *J Am Chem Soc.* 130:1806-7; 2008-20; Hong, J.; Luesch, H. Largazole: from discovery to broad-spectrum therapy. *Nat Prod Rep.* 29:449-56; 2012; Chen, Q. Y.; Liu, Y.; Luesch, H. Systematic Chemical Mutagenesis Identifies a Potent Novel Apratoxin A/E Hybrid with Improved in Vivo Antitumor Activity. *ACS Med Chem Lett.* 2:861-865; 2011]. Additionally, the free radical scavenger fucoxanthin, a carotenoid from a common edible seaweed, *Hijikia fusiformis* [Yon, X.; Chuda, Y.; Suzuki, M.; Nagata, T. Fucoxanthin as the major antioxidant in *Hijikia fusiformis*, a common edible seaweed. *Biosci Biotechnol Biochem.* 63:605-7; 1999], was found to activate the antioxidant defense system (Nrf2/ARE) in mouse liver cells.

However, despite these developments, there exists an unmet need for additional antioxidants and for additional treatments for ROS-mediated diseases. This study follows on previous research that showed that extracts of marine algae can activate the Nrf2-ARE pathway, and that extracts of *Ulva* spp. were particularly active among a variety of seaweeds tested [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013]. As a result of ongoing investigations to identify new drug leads from marine sources, we report seaweed extract compositions isolated from cultivated green alga *Ulva* sp., processes for isolation, enriched active fractions, and isolated active agents. The extracts, enriched active extracts, and compounds herein are found to be activators of the cytoprotective Nrf2-ARE pathway. These findings provide new alternatives for the treatment and/or prevention of reactive oxygen species (ROS)-mediated diseases and diseases alleviated or prevented through the activation of the Nrf2-ARE (antioxidant response element) pathway, such as inflammation, cancer, Alzheimer's disease and other neurodegenerative disorders, stroke, chronic kidney disease, type II diabetes, and aging itself.

BRIEF SUMMARY OF THE INVENTION

This invention is directed towards seaweed extract compositions, enriched active extracts, processes for isolation, isolated active agents, and methods of treating and/or preventing disease, disorders and conditions in a subject, including, reactive oxygen species (ROS)-mediated diseases and diseases alleviated or prevented through the activation of the Nrf2-ARE (antioxidant response element) pathway, including proliferative diseases and disorders, inflammation, Alzheimer's disease and other neurodegenerative disorders, stroke, chronic kidney disease, type II diabetes, and certain diseases and disorders of aging and associated with aging and exposure, by use of the extracts, enriched active extracts, compounds, and compositions thereof.

This invention is directed towards seaweed extract compositions, enriched active extracts, processes for isolation, isolated active agents, methods for activating the Nrf2-ARE pathway, and methods of treating and/or preventing reactive oxygen species (ROS)-mediated diseases and diseases alleviated or prevented through the activation of the Nrf2-ARE (antioxidant response element) pathway, including proliferative diseases and disorders, inflammation, cancer, Alzheimer's disease and other neurodegenerative disorders, stroke, chronic kidney disease, type II diabetes, and aging itself.

Another aspect of this invention is a composition comprising a seaweed extract herein (e.g., extract of *Ulva* sp.). Another aspect is a composition comprising an enriched active extract from a seaweed extract herein. Another aspect is a composition comprising an isolated compound from a seaweed extract herein.

In one embodiment, the compound (or combinations of compounds) delineated herein is obtained from a procedure comprising extraction from seaweed. In certain embodiments, the procedure for use in obtaining the compound (or combinations of compounds) further includes any of isolation, enrichment, evaporation, and partitioning steps of the seaweed extracts.

Another aspect of this invention is a pharmaceutical composition comprising a seaweed extract herein or a compound that occurs in a seaweed extract herein.

In one embodiment, the invention provides an extract from seaweed isolated by:
 a). exposing said seaweed to a solvent or solvent combination;
 b). filtering the material/mixture from step a);
 c). removing the solvent or solvent combination from step b);
 d). purifying the material/mixture from c) using chromatography and collecting fractions;
 e). removing the chromatography mobile phase from d) to provide concentrated fractions.

Another aspect is where the concentrated fractions from step e) are screened in an ARE reporter assay. Another aspect is where the solvent or solvent combination in extraction step a) is selected from the group consisting of ethyl acetate, methanol, hexanes, ethanol, isopropanol, acetonitrile, water, and dichloromethane. Another aspect is where the solvent or solvent combination in extraction step a) is selected from the group consisting of ethyl acetate and ethanol. Another aspect is where steps a)-c) are repeated with the same or different solvent or solvent combination as used in the previous iteration(s). Another aspect is where the seaweed is the green alga *Ulva* sp. Another aspect is where the green alga *Ulva* sp. is cultivated.

In another embodiment, the invention provides an extract from seaweed isolated by:
 [a]. exposing said seaweed to a solvent or solvent combination;
 [b]. filtering the material/mixture from step [a].

Another aspect is where the solvent or solvent combination in extraction step [a] is selected from the group consisting of ethyl acetate, methanol, hexanes, ethanol, isopropanol, acetonitrile, water, and dichloromethane. Another aspect is where the solvent or solvent combination in extraction step [a] is selected from the group consisting of ethyl acetate and ethanol. Another aspect is where steps [a]-[b] are repeated with the same or different solvent or solvent combination as used in the previous iteration(s). Another aspect is where the seaweed is the green alga *Ulva* sp. Another aspect is where the green alga *Ulva* sp. is cultivated.

Another aspect is a compound or extract obtained by one or more steps of the processes or procedures delineated herein, including specifically as delineated in the Examples herein.

Another aspect is where the seaweed extract comprises one or more compounds selected from (6S,7aR)-6-hydroxy-4,4,7a-trimethyl-5,6,7,7a-tetrahydrobenzofuran-2(4H)-one (1), (6S,7aS)-6-hydroxy-4,4,7a-trimethyl-5,6,7,7a-tetrahydrobenzofuran-2(4H)-one (2), (E)-4-((1S,2R,4S)-1,2,4-trihydroxy-2,6,6-trimethylcyclohexyl)but-3-en-2-one (3), and 8-chloro-6,7-dihydroxydeca-2,4-dienal (4).

Another aspect is where the seaweed extract is enriched in one or more compounds selected from (6S,7aR)-6-hydroxy-4,4,7a-trimethyl-5,6,7,7a-tetrahydrobenzofuran-2(4H)-one (1), (6S,7aS)-6-hydroxy-4,4,7a-trimethyl-5,6,7,7a-tetrahydrobenzofuran-2(4H)-one (2), (E)-4-((1S,2R,4S)-1,2,4-trihydroxy-2,6,6-trimethylcyclohexyl)but-3-en-2-one (3), and 8-chloro-6,7-dihydroxydeca-2,4-dienal (4).

Another aspect is where the seaweed extract comprises 8-chloro-6,7-dihydroxydeca-2,4-dienal (4).

In another embodiment the invention provides a compound that is 8-chloro-6,7-dihydroxydeca-2,4-dienal (4).

In another aspect the invention provides an isolated compound that is selected from 8-chloro-6,7-dihydroxydeca-2,4-dienal (4).

In another aspect, the invention provides a pharmaceutical composition comprising a seaweed extract and a pharmaceutically acceptable carrier.

In another aspect, the invention provides a pharmaceutical composition comprising an enriched seaweed extract (e.g., enriched through evaporation, enriched through fractionation, enriched through partial purification) and a pharmaceutically acceptable carrier.

In other aspects, the invention provides a method of treating and/or preventing a disease, disorder, or symptom thereof in a subject, comprising administering to the subject any compound or seaweed extract herein. In another aspect, the compound or seaweed extract is administered in an amount and under conditions sufficient to ameliorate the disease, disorder, or symptom thereof in a subject. In another aspect, the disease, disorder, or symptom includes proliferative diseases and disorders, inflammation, cancer, Alzheimer's disease and other neurodegenerative disorders, stroke, chronic kidney disease, type II diabetes, cancer, tumor growth, cancer of the colon, breast, bone, brain and others (e.g., osteosarcoma, neuroblastoma, colon adenocarcinoma), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders, and aging itself.

In other aspects, the invention provides a method of modulating Nrf2-ARE activity in a subject, comprising contacting the subject with any compound or seaweed extract herein, in an amount and under conditions sufficient to modulate Nrf2-ARE activity. In another aspect, the modulation is activation.

In other aspects, the invention provides a method of modulating the proliferation activity in a subject, comprising contacting the subject with any compound or seaweed extract herein, in an amount and under conditions sufficient to modulate proliferation activity.

In one aspect, the invention provides a method of treating a subject suffering from or susceptible to a proliferation related disorder or disease, comprising administering to the subject an effective amount of a compound or seaweed extract or pharmaceutical composition of any compound or seaweed extract herein.

In another aspect, the invention provides a method of treating a subject suffering from or susceptible to a ROS-mediated disorder or disease, comprising administering to the subject an effective amount of a compound or seaweed extract or pharmaceutical composition of any compound or seaweed extract herein.

In another aspect, the invention provides a method of treating a subject suffering from or susceptible to a disorder or disease alleviated or prevented through the Nrf2-ARE pathway, comprising administering to the subject an effective amount of a compound or seaweed extract or pharmaceutical composition of any compound or seaweed extract herein. Another aspect is where the disorder or disease alleviated or prevented through the Nrf2-ARE pathway includes proliferative diseases and disorders, inflammation, cancer, Alzheimer's disease and other neurodegenerative disorders, stroke, chronic kidney disease, type II diabetes, cancer, tumor growth, cancer of the colon, breast, bone, brain and others (e.g., osteosarcoma, neuroblastoma, colon adenocarcinoma), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, (fibro)proliferative disorders, and aging itself.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, an effective amount of a compound or seaweed extract or pharmaceutical composition of any compound or seaweed extract herein, such that said subject is treated for said disorder.

In another aspect, the invention provides a method of treating a subject suffering from or susceptible to a ROS activity related disorder or disease, wherein the subject has been identified as in need of treatment for a ROS-related disorder or disease, comprising administering to said subject in need thereof, an effective amount of a compound or or seaweed extract or pharmaceutical composition of any compound or seaweed extract herein, such that said subject is treated for said disorder.

In another aspect, the invention provides a method of treating a subject suffering from or susceptible to a Nrf2-ARE activity related disorder or disease, wherein the subject has been identified as in need of treatment for a Nrf2-ARE related disorder or disease, comprising administering to said subject in need thereof, an effective amount of a compound or seaweed extract or pharmaceutical composition of any compound or seaweed extract herein, such that said subject is treated for said disorder. Another aspect is where the said disorder includes proliferative diseases and disorders, inflammation, cancer, Alzheimer's disease and other neurodegenerative disorders, stroke, chronic kidney disease, type II diabetes, and aging itself.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, an effective amount of a compound or seaweed extract or pharmaceutical composition of any compound or seaweed extract herein, such that cell proliferation in said subject is modulated (e.g., down regulated). In another aspect, the compounds or seaweed extracts delineated herein preferentially target cancer cells over nontransformed cells.

In a specific aspect, the invention provides a method of treating and/or preventing cancer, tumor growth, cancer of the colon, breast, bone, brain and others (e.g., osteosarcoma, neuroblastoma, colon adenocarcinoma), comprising administering to said subject in need thereof, an effective amount of any compound or seaweed extract delineated herein, and pharmaceutically acceptable salts thereof. Other cancers that may be treated and/or prevented by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated and/or prevented include the treatment of inflammatory disorders, neurodegenerative diseases, protozoal and latent viral infections, and (fibro)proliferative disorders.

In a specific aspect, the invention provides a method of treating and/or preventing inflammation, Alzheimer's disease and other neurodegenerative disorders, stroke, chronic kidney disease, type II diabetes, aging itself, and other diseases mediated through ROS, comprising administering to said subject in need thereof, an effective amount of any compound or seaweed extract delineated herein, and pharmaceutically acceptable salts thereof.

In another aspect, the invention provides a method of treating and/or preventing diseases, disorders, or symptoms thereof mediated by activation of the Nrf2-ARE pathway in a subject in need thereof comprising administering to said subject, an effective amount of any compound or seaweed extract delineated herein, and pharmaceutically acceptable salts thereof.

In another aspect, the invention provides a method of treating and/or preventing diseases, disorders, or symptoms in a subject in need thereof comprising administering to said subject, an effective amount of any compound or seaweed extract delineated herein, and pharmaceutically acceptable salts thereof. Such methods are useful for treating and/or preventing memory loss, inducing neurogenesis, enhancing memory retention, enhancing memory formation, increasing synaptic potential or transmission, or increasing long term potentiation (LTP). Such methods are also useful for treating and/or preventing diseases and disorders associated with stem cell fate and that are affected by differentiation, dedifferentiation or transdifferentiation, and thus include but not limited to myogenesis, neurogenesis, osteogenesis and osteoblast maturation.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which:

FIG. 10. depicts the activation of ARE reporter and induction of endogenous Nqo1 transcript levels in vivo 12 h after gavage-feeding of *Ulva* extract mixtures.

FIG. 11. depicts the chemical analysis and biological characterization of purified active components.

DETAILED DESCRIPTION

Definitions

Figure 1:
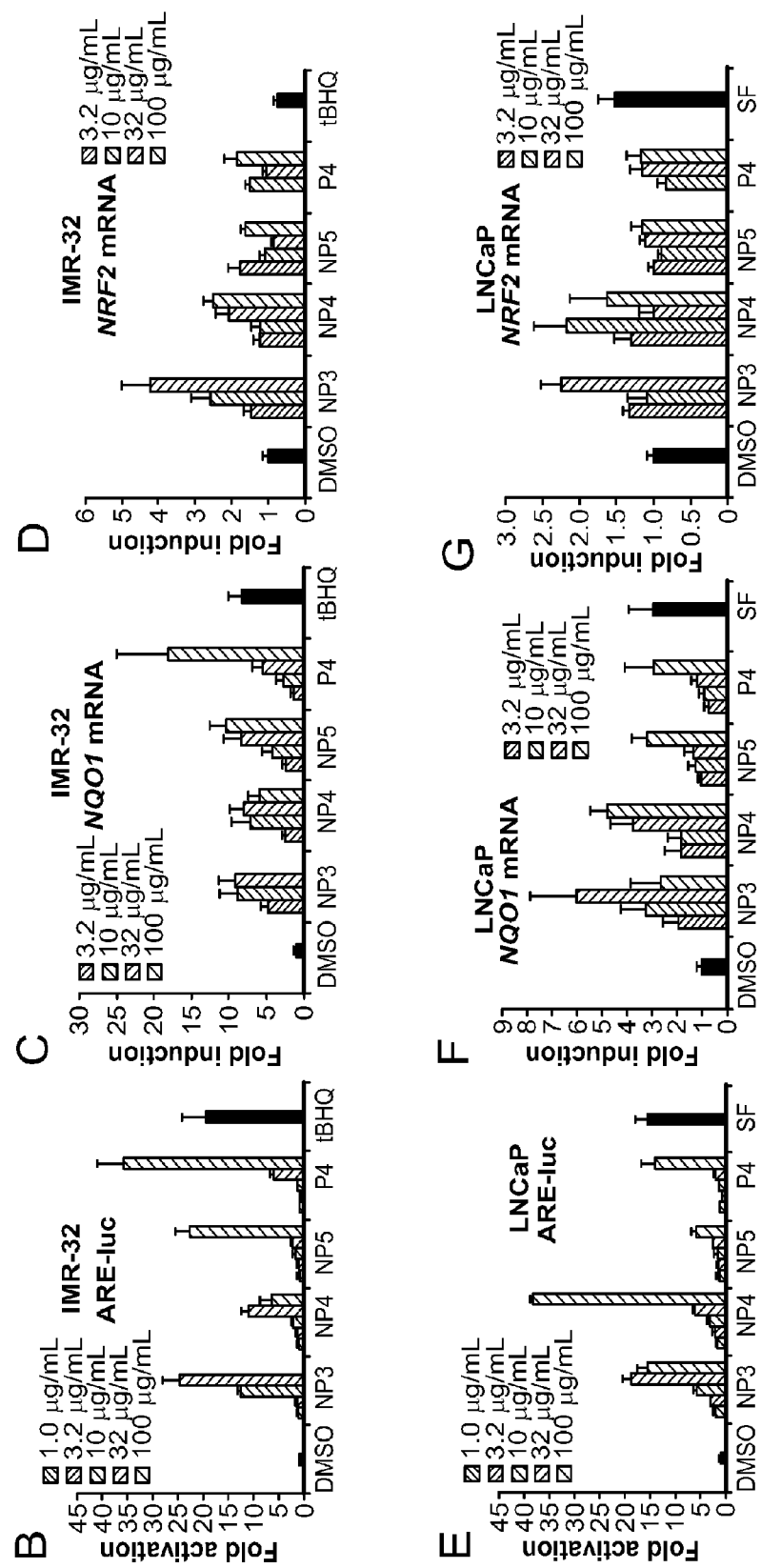
FIG. 1. depicts the extraction and fractionation of cultivated *Ulva* sp. and assessment of ARE-related transcriptional effects in neuroblastoma and prostate cancer cells.
Figure 2:
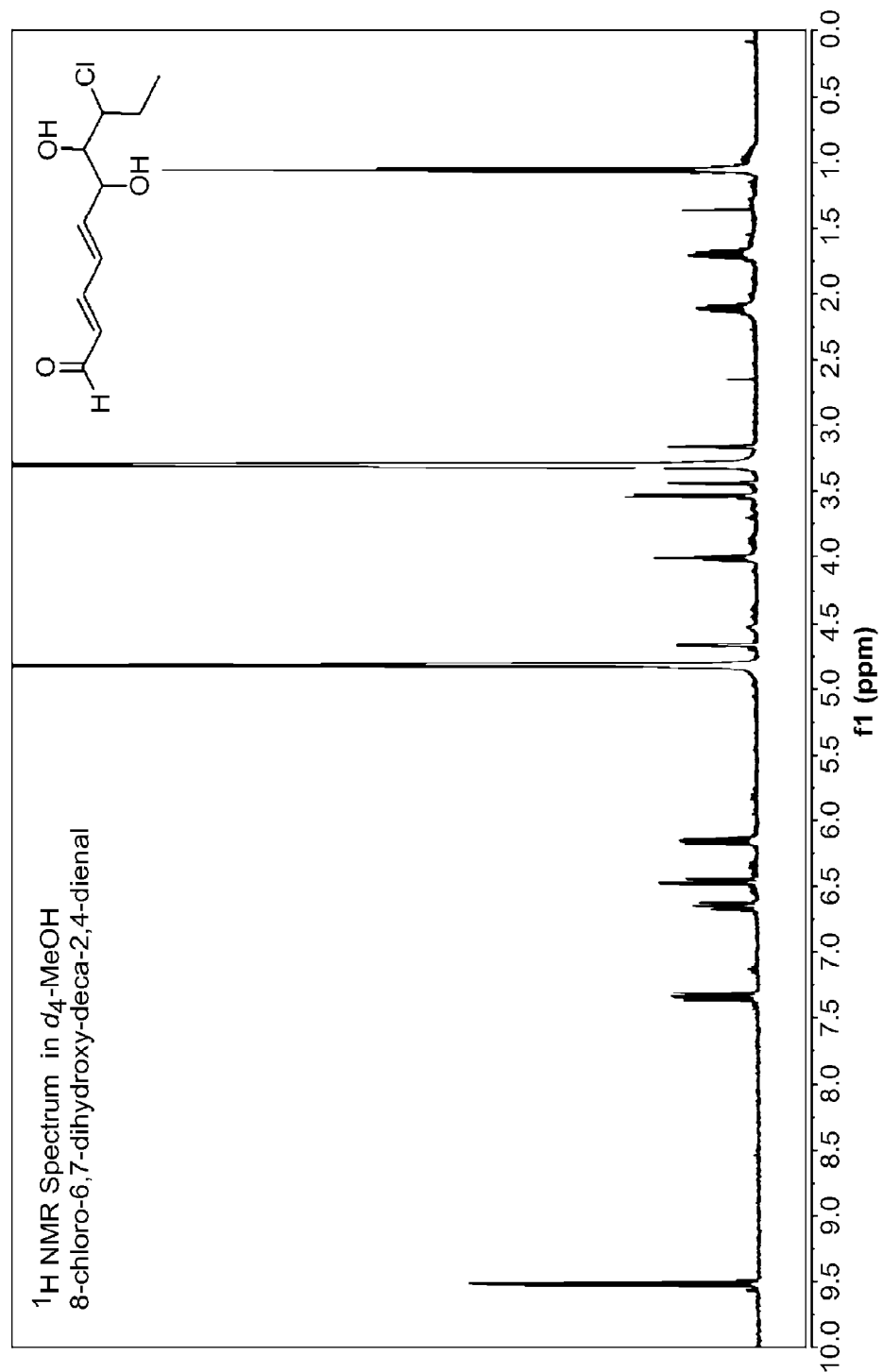
FIG. 2. depicts the $^1$H NMR spectrum of 8-chloro-6,7-dihydroxy-deca-2,4-dienal (4) in $d_4$-MeOH.
Figure 3:
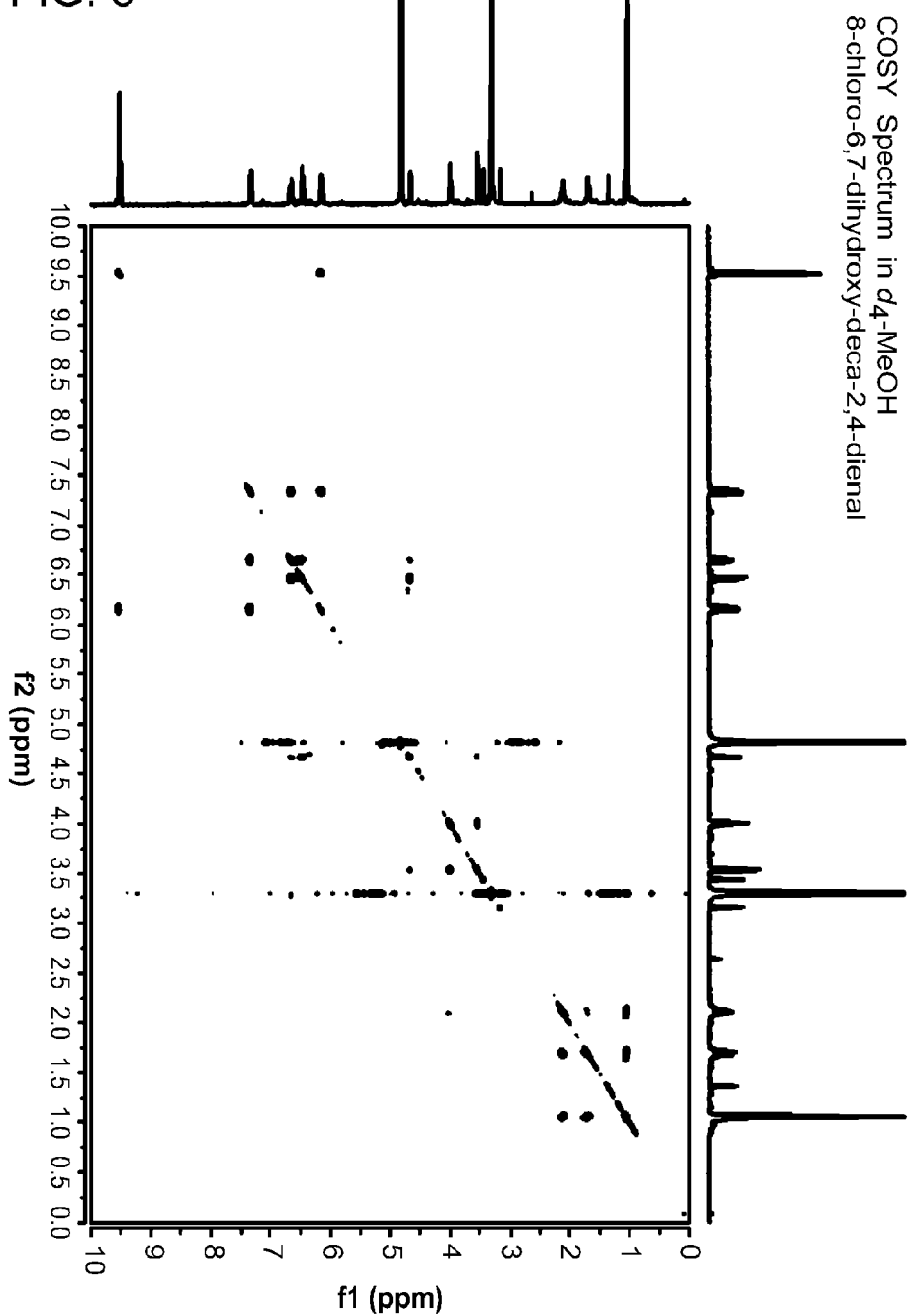
FIG. 3. depicts the COSY spectrum of 8-chloro-6,7-dihydroxy-deca-2,4-dienal (4) in $d_4$-MeOH.
Figure 4:
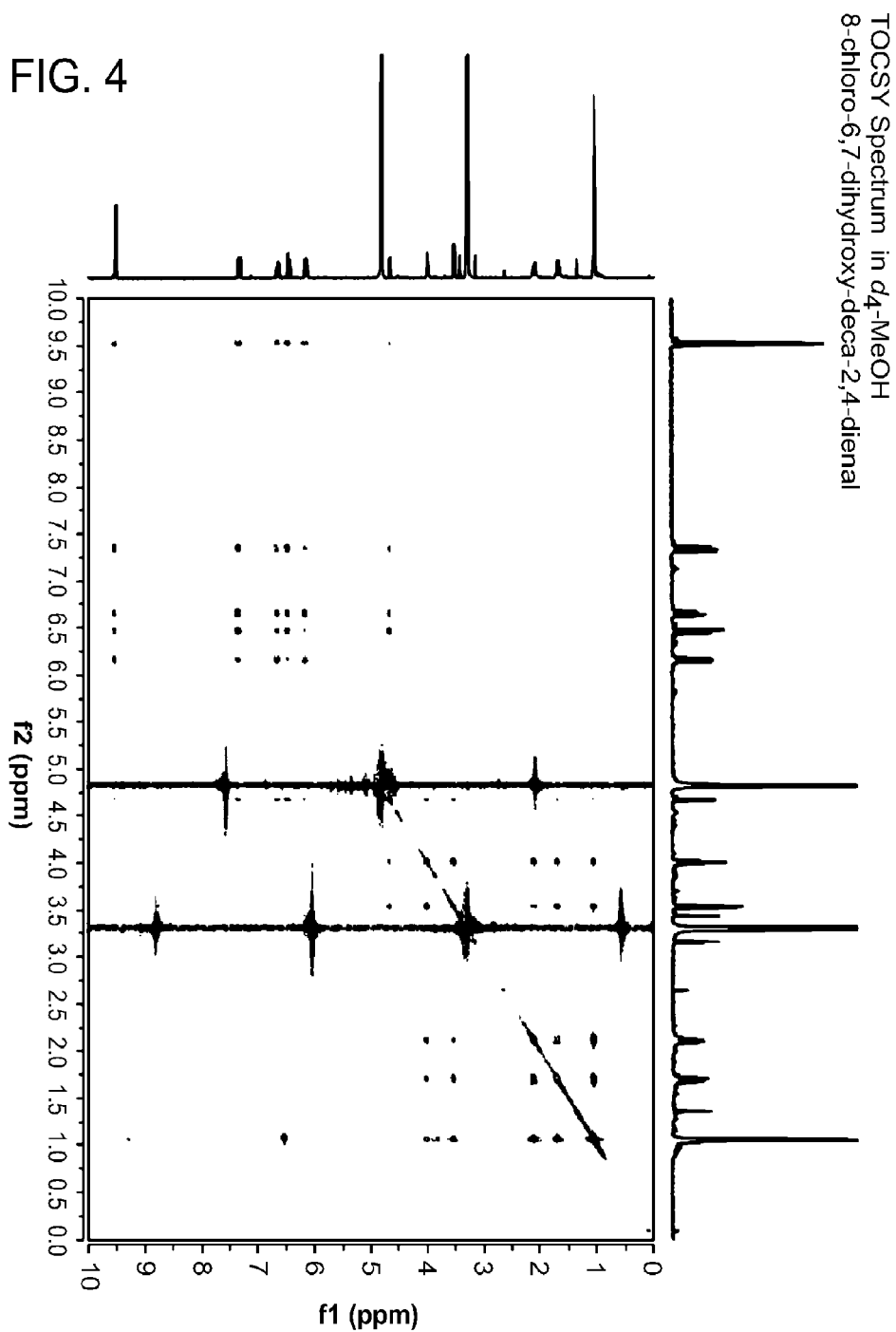
FIG. 4. depicts the TOCSY spectrum of 8-chloro-6,7-dihydroxy-deca-2,4-dienal (4) in $d_4$-MeOH.
Figure 5:
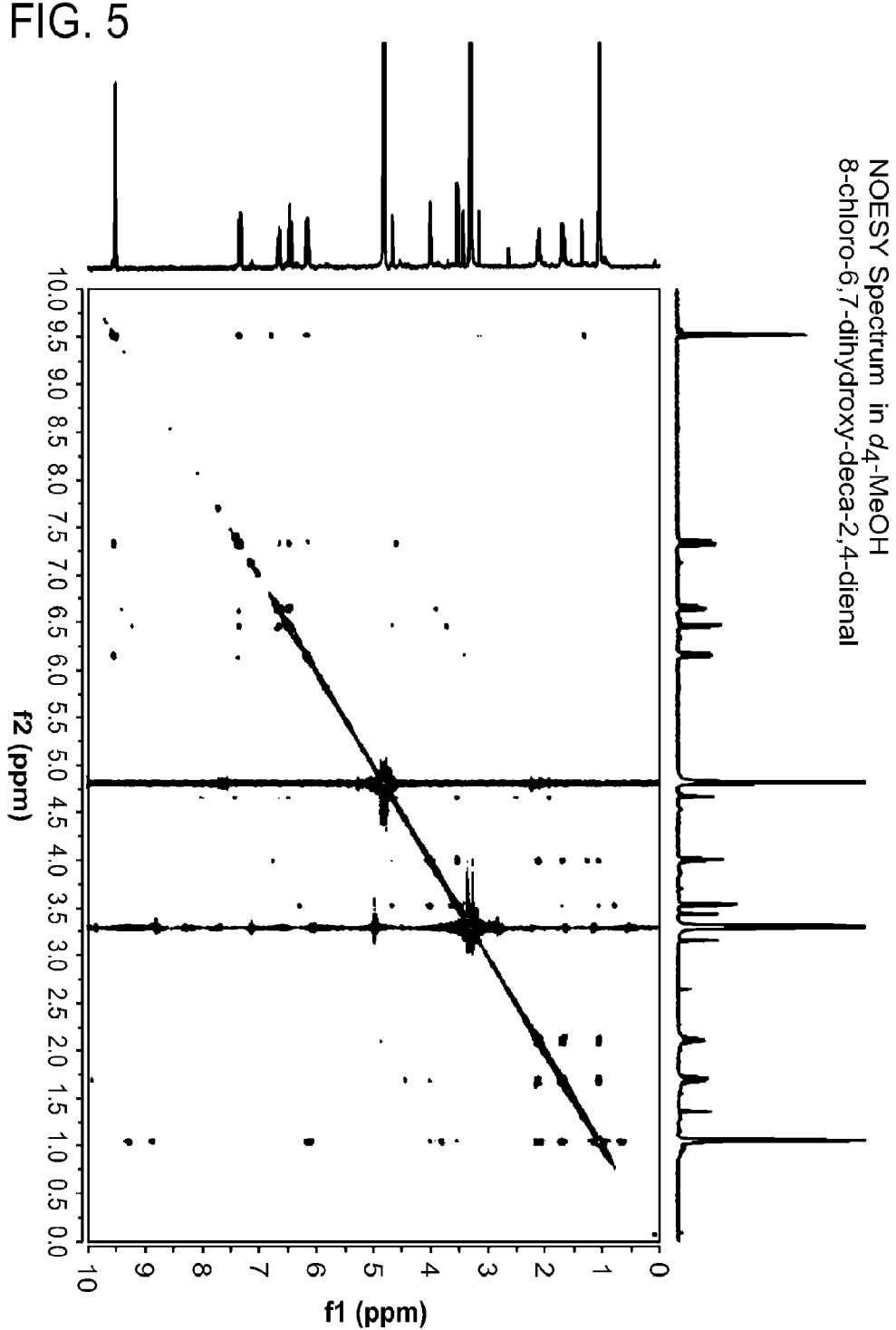
FIG. 5. depicts the NOESY spectrum of 8-chloro-6,7-dihydroxy-deca-2,4-dienal (4) in $d_4$-MeOH.
Figure 6:
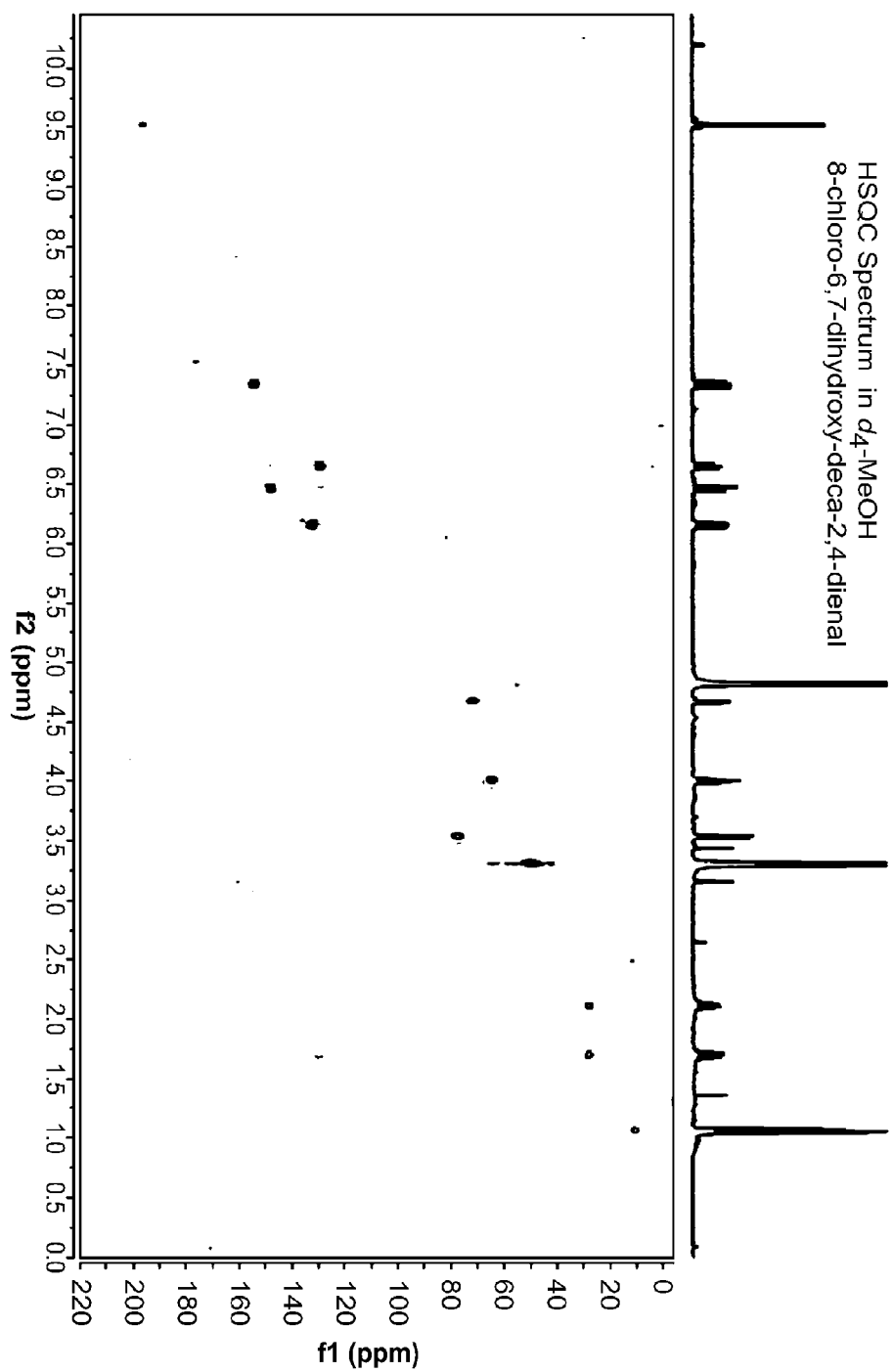
FIG. 6. depicts the HSQC spectrum of 8-chloro-6,7-dihydroxy-deca-2,4-dienal (4) in $d_4$-MeOH.
Figure 7:
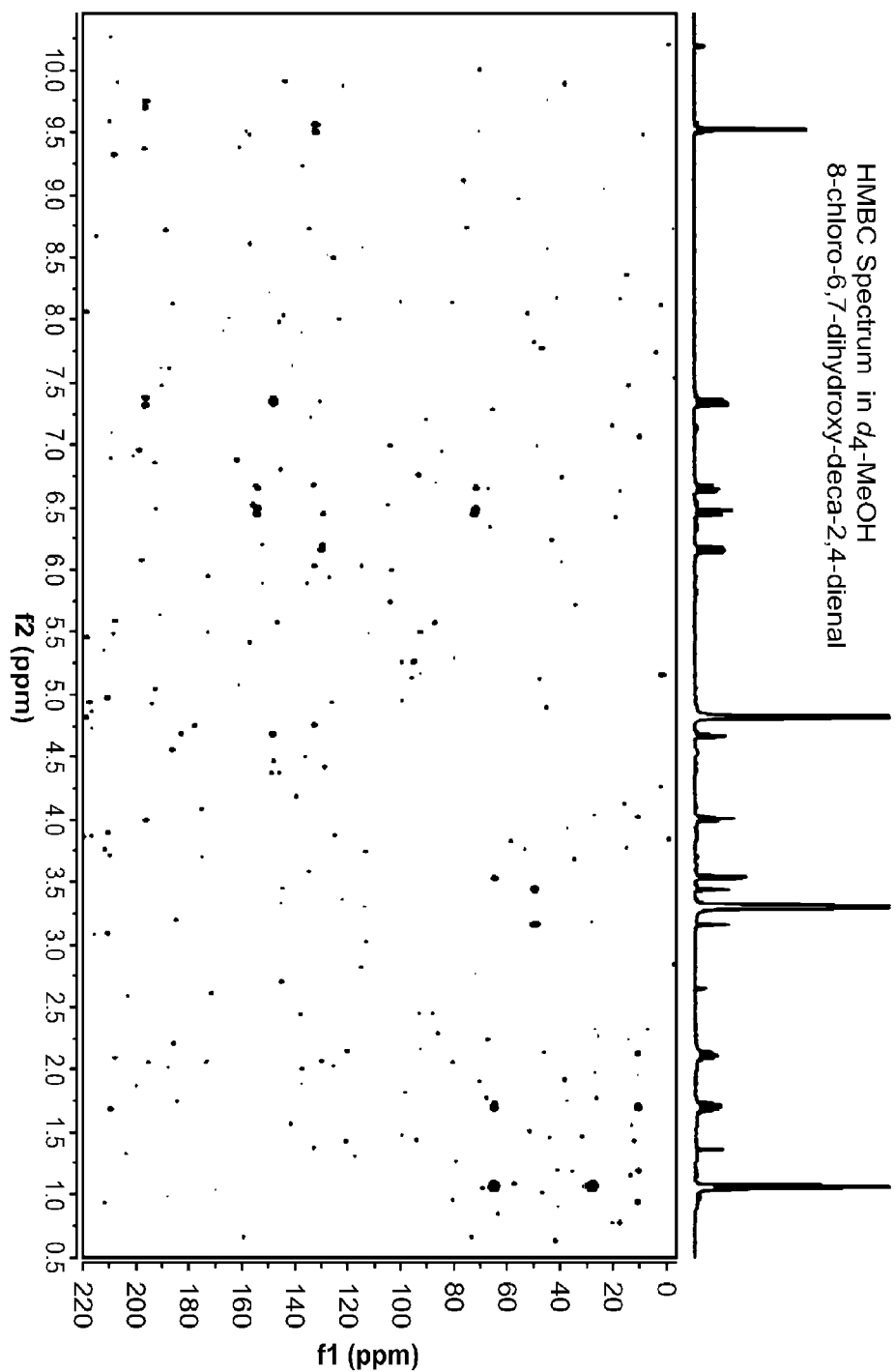
FIG. 7. depicts the HMBC spectrum of 8-chloro-6,7-dihydroxy-deca-2,4-dienal (4) in $d_4$-MeOH.
Figure 8:
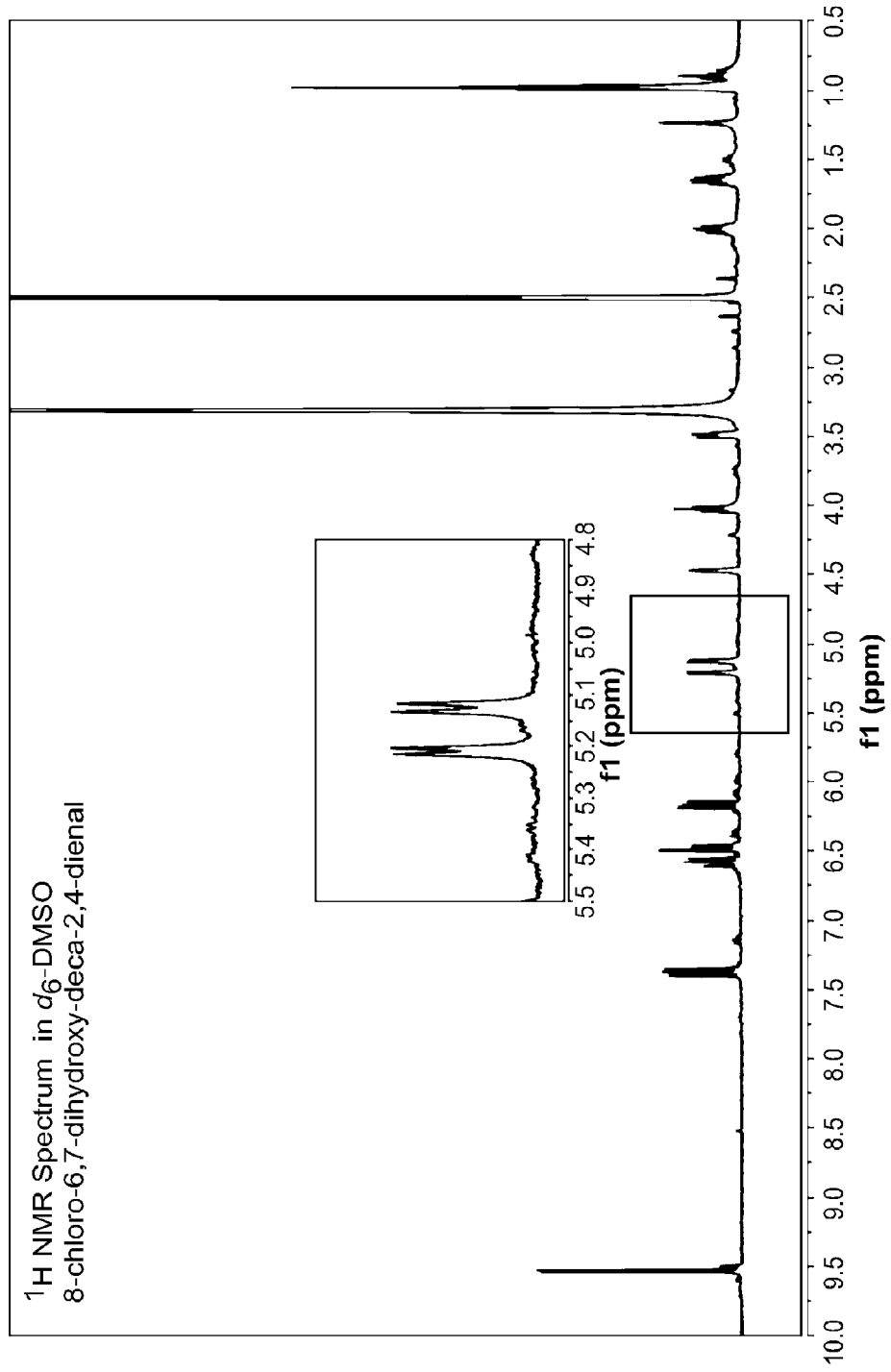
FIG. 8. depicts the $^1$H NMR spectrum of 8-chloro-6,7-dihydroxy-deca-2,4-dienal (4) in $d_6$-DMSO.

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression.

As used herein, "activating" encompasses permitting, increasing and enhancing progression.

As used herein, "enriched" encompasses greater or increased amounts of a material or desired or active compound or agent relative to its natural or other reference state.

As used herein, as "extract" is a preparation of constituents of a material (e.g., seaweed), including for example, solvent extracts, concentrated forms of said constituents, concentrated solvent extracts, isolated chemical compounds or mixtures thereof.

The term "modulate" refers to increases or decreases in the activity of a cell in response to exposure to a compound of the invention.

The terms "cultivated," "cultivate," and "cultivation" refer to material that is grown under controlled conditions or the process of growing material under controlled conditions. This material also refers to those obtained or purchased that were grown under controlled conditions.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 1000 mg/kg, preferably about 0.1 mg/kg to about 1000 mg/kg, more preferably about 10 mg/kg to about 500 mg/kg of body weight. In other embodiments, the therapeutically effective amount may range from about 0.10 nM to about 500 μM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds (e.g., isolated compounds, compounds within seaweed extracts, compounds fractionated from seaweed extracts) of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, 2$^{nd}$ Edition, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

The present invention also contemplates solvates (e.g., hydrates) of a compound of herein, compositions thereof, and their use in the treatment and/or prevention of reactive oxygen species (ROS)-mediated diseases and diseases alleviated or prevented through the activation of the Nrf2-ARE (antioxidant response element) pathway. As used herein, "solvate" refers to the physical association of a compound of the invention with one or more solvent or water molecules, whether organic or inorganic. In certain instances, the solvate is capable of isolation, for example, when one or more solvate molecules are incorporated in the crystal lattice of the crystalline solid.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

This invention is directed towards seaweed extract compositions, enriched active fractions, processes for isolation, isolated active agents, and methods of treating and/or preventing diseases and disorders by use of the extracts, compounds, and compositions delineated herein.

In other aspects, the invention provides a method of treating and/or preventing a disease, disorder, or symptom thereof in a subject, comprising administering to the subject any compound or seaweed extract herein. In another aspect, the compound is administered in an amount and under conditions sufficient to ameliorate the disease, disorder, or symptom thereof in a subject.

The methods can further comprise that wherein the composition is an extract of *Ulva* sp. or an isolated compound that occurs in a seaweed extract herein.

Another aspect is where the seaweed extract comprises one or more compounds selected from the group consisting of (6S,7aR)-6-hydroxy-4,4,7a-trimethyl-5,6,7,7a-tetrahydrobenzofuran-2(4H)-one (1), (6S,7aS)-6-hydroxy-4,4,7a-trimethyl-5,6,7,7a-tetrahydrobenzofuran-2(4H)-one (2), (E)-4-41S,2R,4S)-1,2,4-trihydroxy-2,6,6-trimethylcyclohexyl)but-3-en-2-one (3), and 8-chloro-6,7-dihydroxydeca-2,4-dienal (4). Another aspect is where the seaweed extract comprises 8-chloro-6,7-dihydroxydeca-2,4-dienal (4).

In another aspect the invention provides an isolated compound that is 8-chloro-6,7-dihydroxydeca-2,4-dienal (4).

In other aspects, the invention provides a method of modulating Nrf2-ARE activity in a subject, comprising contacting the subject with any compound or seaweed extract herein, in an amount and under conditions sufficient to modulate Nrf2-ARE activity. In another aspect, the modulation is activation.

In other aspects, the invention provides a method of modulating the proliferation activity in a subject, comprising contacting the subject with any compound or seaweed extract herein, in an amount and under conditions sufficient to modulate proliferation activity.

In one aspect, the invention provides a method of treating a subject suffering from or susceptible to a proliferation related disorder or disease, comprising administering to the subject an effective amount of a compound or seaweed extract or pharmaceutical composition of any compound or seaweed extract herein.

In another aspect, the invention provides a method of treating a subject suffering from or susceptible to a ROS-mediated disorder or disease, comprising administering to the subject an effective amount of a compound or seaweed extract or pharmaceutical composition of any compound or seaweed extract herein.

In another aspect, the invention provides a method of treating a subject suffering from or susceptible to a disorder or disease alleviated or prevented through the Nrf2-ARE pathway, comprising administering to the subject an effective amount of a compound or seaweed extract or pharmaceutical composition of any compound or seaweed extract herein.

Another aspect is where the seaweed is the green alga *Ulva* sp.

In certain embodiments, the invention provides a method as described above, wherein the seaweed extract comprises one or more compounds selected from the group consisting of (6S,7aR)-6-hydroxy-4,4,7a-trimethyl-5,6,7,7a-tetrahydrobenzofuran-2(4H)-one (1), (6S,7aS)-6-hydroxy-4,4,7a-trimethyl-5,6,7,7a-tetrahydrobenzofuran-2(4H)-one (2), (E)-4-((1S,2R,4S)-1,2,4-trihydroxy-2,6,6-trimethylcyclohexyl)but-3-en-2-one (3), and 8-chloro-6,7-dihydroxydeca-2,4-dienal (4).

In certain embodiments, the invention provides a method of treating and/or preventing a disorder, wherein the disorder is proliferative diseases and disorders, inflammation, cancer, Alzheimer's disease and other neurodegenerative disorders, stroke, chronic kidney disease, type II diabetes, and aging itself, and other diseases mediated through ROS or alleviated or prevented through the Nrf2-ARE pathway.

In certain embodiments, the methods are useful in providing and/or enhancing anti-aging properties of skin by preventing (e.g., UVA-induced, UVB-induced, photo-damage, aging) wrinkle formation. In certain embodiments, the methods herein are useful in providing and/or enhancing skin tone and skin appearance properties of skin by administration of a topical formulation of compounds and compositions herein to the skin.

In certain embodiments, the compounds and compositions herein are useful in providing and/or enhancing anti-aging properties of skin by preventing (e.g., UVA-induced, UVB-induced, photo-damage, aging) wrinkle formation. In certain embodiments, the compounds and compositions herein are useful in providing and/or enhancing skin tone and skin appearance properties of skin by administration of a topical formulation to the skin.

In certain embodiments, the subject is a mammal, preferably a primate or human.

In another embodiment, the invention provides a method as described above, wherein the effective amount of the compound or seaweed extract ranges from about 0.005 µg/kg to about 500 mg/kg, preferably about 0.1 mg/kg to about 500 mg/kg, more preferably about 10 mg/kg to about 500 mg/kg of body weight.

In other embodiments, the invention provides a method as described above wherein the effective amount of the compound or seaweed extract ranges from about 1.0 nM to about 500 µM. In another embodiment, the effective amount ranges from about 100 nM to about 100 µM.

In other embodiments, the invention provides a method as described above wherein the effective amount of the compound or seaweed extract ranges from about 0.1 mg/ml to about 1000 mg/ml. In certain embodiments, the effective amount ranges from about 1.0 mg/ml to about 500 mg/ml. In another embodiment, the effective amount ranges from about 1.0 mg/ml to about 100 mg/ml.

In another embodiment, the invention provides a method as described above, wherein the compound or seaweed extract is administered intravenously, intramuscularly, subcutaneously, intracerebroventricularly, orally or topically.

In another embodiment, the invention provides a method as described herein wherein the compound or seaweed extract demonstrates selectivity (e.g., at least 2-fold, at least 5-fold, at least 10-fold, at least X-fold where X is any number between 1 and 20 inclusive) in cell growth activity (e.g., in transformed/nontransformed, MDA-MB-231/NMuMG, U2OS/NIH3T3 cells). In another aspect, the compound or seaweed extract demonstrates selectivity in modulating cell growth activity (e.g., at least 2-fold, at least 5-fold, at least 10-fold, at least X-fold where X is any number between 1 and 20 inclusive) relative to another standard anticancer therapy (e.g., paclitaxel, actinomycin D, doxorubicin).

In other embodiments, the invention provides a method as described above, wherein the compound or seaweed extract is administered alone or in combination with one or more other therapeutics. In a further embodiment, the additional therapeutic agent is an anti-cancer agent, chemotherapeutic agent, an anti-angiogenesis agent, cytotoxic agent, or an anti-proliferation agent. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, The Merck Manual of Diagnosis and Therapy, 15th Ed., pp. 1206-1228, Berkow et al., eds., Rahay, N. J., 1987).

Another object of the present invention is the use of a compound or seaweed extract as described herein (e.g., of any formulae herein) in the manufacture of a medicament for use in the treatment and/or prevention of a cell proliferation disorder or disease, or to affect cell differentiation, dedifferentiation or transdifferentiation. Another object of the present invention is the use of a compound or seaweed extract as described herein (e.g., of any formulae herein) for use in the treatment and/or prevention of a cell proliferation disorder or disease, or affect cell differentiation, dedifferentiation or transdifferentiation.

Another object of the present invention is the use of a compound or seaweed extract as described herein (e.g., of any formulae herein) for use in the treatment and/or prevention of a ROS-mediated disorder or disease, or a disease alleviated or prevented through the Nrf2-ARE pathway. Another object of the present invention is where the disease or disorder includes proliferative diseases and disorders, inflammation, cancer, Alzheimer's disease and other neurodegenerative disorders, stroke, chronic kidney disease, type II diabetes, and aging itself, and other diseases mediated through ROS or alleviated or prevented through the Nrf2-ARE pathway.

Pharmaceutical Compositions

In one aspect, the invention provides a pharmaceutical composition comprising the compound or seaweed extract and a pharmaceutically acceptable carrier.

In one embodiment, the invention provides a pharmaceutical composition wherein the compound or seaweed extract is selected from the group consisting of (6S,7aR)-6-hydroxy-4,4,7a-trimethyl-5,6,7,7a-tetrahydrobenzofuran-2(4H)-one (1), (6S,7a5)-6-hydroxy-4,4,7a-trimethyl-5,6,7,7a-tetrahydrobenzofuran-2(4H)-one (2), (E)-4-((1S,2R,4S)-1,2,4-trihydroxy-2,6,6-trimethylcyclohexyl)but-3-en-2-one (3), and 8-chloro-6,7-dihydroxydeca-2,4-dienal (4), and a pharmaceutically acceptable carrier.

In another embodiment, the invention provides a pharmaceutical composition wherein the compound or seaweed extract is an extract from the green alga *Ulva* sp., and a pharmaceutically acceptable carrier.

In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound or seaweed extract, in unit dosage form, together with instructions for administering the compound to a subject suffering from or susceptible to a ROS mediated disease or disorder, including proliferative diseases and disorders, inflammation, cancer, stroke, chronic kidney disease, type II diabetes, and aging itself, and other diseases mediated through ROS or alleviated or prevented through the Nrf2-ARE pathway, Alzheimer's disease and other neurodegenerative disorders, memory loss, inducing neurogenesis, enhancing memory retention, enhancing memory formation, increasing synaptic potential or transmission, or increasing long term potentiation (LTP), etc.

In one aspect, the invention provides a kit comprising an effective amount of a compound or seaweed extract, in unit dosage form, together with instructions for administering the compound to a subject suffering from or susceptible to a cell proliferation disease or disorder, including cancer, solid tumor, angiogenesis, etc.

In one aspect, the invention provides a kit comprising an effective amount of a compound or seaweed extract, in unit dosage form, together with instructions for administering the compound to a subject suffering from or susceptible to a disease or disorder alleviated or prevented through the Nrf2-ARE pathway, including proliferative diseases and disorders, inflammation, cancer, stroke, chronic kidney disease, type II diabetes, and aging itself, and other diseases mediated through ROS or alleviated or prevented through the Nrf2-ARE pathway, Alzheimer's disease and other neurodegenerative disorders, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *theobroma*; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and *echinacea*, for example. Wetting agents and lubricants such as sodium lauryl sulfate, as well as coloring agents, flavoring agents, lubricants, excipients, tableting agents, stabilizers, anti-oxidants and preservatives, can also be present.

Topical administration of the pharmaceutical compositions of this invention is especially useful when the desired treatment involves areas or organs readily accessible by topical application. For topical application topically to the skin, the pharmaceutical composition should be formulated with a suitable ointment, lotion, or cream containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

For topical administration, the active compound(s), extracts, enriched extracts, or prodrug(s) can be formulated as solutions, gels, ointments, creams, suspensions, and the like.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

General Experimental Procedures

Cell culture media, Dulbecco's Modified Eagle Medium (DMEM), and Eagle's Minimum Essential Medium (EMEM) were purchased from Invitrogen (Carlsbad, Calif.), RPMI 1640 from Fisher Scientific (Pittsburgh, Pa.) and fetal bovine serum (FBS) purchased from HyClone (Logan, Utah). Tert-butylhydroquinone (tBHQ) was purchased from Acros Organics (St. Louis, Mo.) and sulforaphane from Sigma (St. Louis, Mo.). FUGENE HD transfection reagent was purchased from Roche Diagnostics (Indianapolis, Ind.), Opti-MEM reduced serum medium from Invitrogen and siLentFect from Bio-Rad laboratories (Hercules, Calif.). BriteLite reagent for ARE reporter assay was purchased from PerkinElmer, Life and Analytical Sciences, Inc. (Waltham, Mass.). IMR-32 neuroblastoma cells, LNCaP human prostate carcinoma cells and the mouse macrophagic cell line RAW264.7 were purchased from American Type Culture Collection (Manassas, Va.). DMSO and Cremophor® EL used for animal work and purchased from Sigma-Aldrich (St Louis, Mo.) were either USP grade or filtered through 5μ filter before use as a vehicle in feeding experiments. All other chemicals and solvents used for extraction, fractionation and isolation of compounds were purchased from Fisher Scientific unless specified.

Optical rotations were measured on a Perkin-Elmer 341 polarimeter. 1H and 2D NMR spectra for compounds were recorded in $CDCl_3$, DMSO-$d_6$ or $CD_3OD$ on a Bruker Avance II 600 MHz spectrometer equipped with a 5 mm TXI cryogenic probe or Bruker Avance 500 MHz spectrometer equipped with a 2.5 mm TXI probe, using residual solvent signals as internal reference. HSQC and HMBC experiments were optimized for $^1JCH=145$ Hz, $^nJCH=7$ Hz respectively. Other $^1H$ NMR spectra were recorded on a Varian 400 MHz spectrometer. $^{13}C$ NMR experiments were recorded on a Bruker 500 MHz or Varian 400 MHz spectrometer (5 mm probe), operating at 125 MHz and 100 MHz, respectively. HRMS data were obtained using an Agilent LC-TOF mass spectrometer equipped with an APCI/ESI multimode ion source, and low-resolution mass spectra were obtained on an A3200 Q TRAP LC/MS/MS (hybrid triple quadrupole linear ion trap mass spectrometer, Applied Biosystems, USA) with an electrospray ionization (ESI) interface operated in positive mode. HPLC-based compound isolation was performed on a Shimadzu LC-20AT Prominence LC system with peak detection by a Shimadzu SPD-M20A Prominence diode array detector.

Example 1: Extraction and Isolation of Enriched Extracts and Compounds 1, 2, 3, and 4 from Cultivated *Ulva* sp Cultivated *Ulva* sp. (2230.8 g) was purchased on Jun. 1, 2010 at Harbor Branch Oceanographic Institute at Florida Atlantic University and freeze-dried. The cultivated *Ulva* sp. was extracted in 200×(w/v) of a non-polar solvent (EtOAc, NP) and subsequently in 200×(w/v) of a polar solvent (EtOH, P) at room temperature for 24 h. At the end of each extraction, the mixture was filtered and the solvents were removed by a Rotavapor® (BÜCHI Labortechnik AG). The resulting extracts were stored at 4° C. until used. The dried non-polar (NP) extract (14.07 g) was then purified via flash silica gel (230-400 mesh, Selecto Scientific, Cat. No. 05719825) chromatography where six 250 ml-fractions were collected using the following solvent systems: 20% EtOAc/Hex, 50% EtOAc/Hex, 75% EtOAc/Hex, 100% EtOAc, 20% MeOH/EtOAc, and 100% MeOH. Each fraction was concentrated to dryness and stored at −20° C. until used to yield: NP1 (184 mg), NP2 (214 mg), NP3 (425 mg), NP4 (130 mg), NP5 (355 mg), and NP6 (4.18 g).

The dried polar (P) extract was purified via C18 reverse-phase chromatography (Davisil® 35-60 mesh, Grace Cat. No. 5134095) where six 200 ml-fractions were collected using the following solvent systems: 100% water, 75% water/MeOH, 50% water/MeOH, 25% water/MeOH, 100% MeOH, and 100% EtOAc. Each fraction was concentrated to dryness and stored at −20° C. until used to yield: P1, P2, P3 (276 mg), P4 (420 mg), P5, and P6 (844 mg).

The six NP and six P fractions were profiled in ARE Luciferase reporter assays in IMR-32 and LNCaP cells, identifying NP3, NP4, NP5, and P4 fractions as the most active fractions (FIGS. 1B and 1E). Each of the four prioritized fractions was chromatographed further employing size exclusion chromatography (Sephadex LH20), and subsequently by several sequences of reverse-phase HPLC as described below. The resulting LH20 chromatography (eluent: 1:1 DCM/MeOH) fractions (1-8) of NP3 (100 mg) were analyzed by $^1$H NMR and LCMS. Supplementary LH20 chromatography (eluent: 2:5:1 Hexanes/DCM/MeOH) and subsequent purification by semipreparative reversed-phase HPLC (Phenomenex Phenyl-Hexyl, 250×10 mm, 4 µm; flow rate, 2.0 mL/min) using a linear gradient of MeOH/$H_2O$ (40%-100% MeOH in 20 min and then 100% MeOH for 10 min) of fraction 7 afforded three compounds after solvent removal: (6S,7aR)-6-hydroxy-4,4,7a-trimethyl-5,6,7,7a-tetrahydrobenzofuran-2(4H)-one (1, $t_R$ 16.3 min, 0.7 mg), (6S,7aS)-6-hydroxy-4,4,7a-trimethyl-5,6,7,7a-tetrahydrobenzofuran-2(4H)-one (2, $t_R$ 14.4 min, 0.7 mg), and (E)-4-((1S,2R,4S)-1,2,4-trihydroxy-2,6,6-trimethylcyclohexyl)but-3-en-2-one (3, $t_R$ 15.5 min, 1.2 mg). Purification of fraction 8 utilizing similar chromatographic conditions afforded 8-chloro-6,7-dihydroxydeca-2,4-dienal (4, $t_R$ 17.9 min, 0.24 mg). The three remaining prioritized fractions were chromatographed under similar LH20 conditions (eluent: 1:1 DCM/MeOH) and fractions assessed for the respective chemical profiles based on $^1$H NMR and HPLC-DAD analyses.

(6S,7aR)-6-hydroxy-4,4,7a-trimethyl-5,6,7,7a-tetrahydrobenzofuran-2(4H)-one (1)

Colorless amorphous solid; $[\alpha]^{20}_D$ −52 (c 0.06, $CHCl_3$); HRESIMS m/z $[M+Na]^+$ 219.0990 (calcd for $C_{11}H_{16}NaO_3$, 219.0997).

(6S,7aS)-6-hydroxy-4,4,7a-trimethyl-5,6,7,7a-tetrahydrobenzofuran-2(4H)-one (2)

Colorless amorphous solid; $[\alpha]^{20}_D$ +44 (c 0.1, $CHCl_3$); HRESIMS m/z $[M+Na]^+$ 219.0988 (calcd for $C_{11}H_{16}NaO_3$, 219.0997).

(E)-4-((1S,2R,4S)-1,2,4-trihydroxy-2,6,6-trimethylcyclohexyl)but-3-en-2-one (3)

Colorless amorphous solid; $[\alpha]^{20}_D$ −68 (c 0.09, MeOH); HRESIMS m/z $[2M+Na]^+$ 507.3286 (calcd for $C_{26}H_{44}NaO_8$, 507.2934) and $[M-H_2O+Na]^+$ 247.1314 (calcd for $C_{13}H_{20}NaO_3$, 247.1310).

8-chloro-6,7-dihydroxydeca-2,4-dienal (4)

Colorless oil; $[\alpha]^{20}_D$ −188 (c 0.0008, MeOH); $^1$H and 2D NMR (500 MHz, $CD_3OD$) data and spectra, see Table 1 and FIGS. 2-8; HRESIMS m/z $[M+Cl]^-$ 253.0404, 255.0376 (ratio 9:6, calcd for $C_{10}H_{15}{}^{35}Cl_2O_3$, 253.0398; $C_{10}H_{15}{}^{37}Cl_2O_3$, 255.0369).

TABLE 1

NMR (500 MHz) data for 8-chloro-6,7-dihydroxy-deca-2,4-dienal (4) in $CD_3OD$

| | $\delta_H$ (J in Hz) | $\delta_C{}^b$ | COSY | HMBC |
|---|---|---|---|---|
| 1 | 9.53, d (8.0) | 196.4, CH | H-2 | C-2 |
| 2 | 6.15, dd (15.0, 8.0) | 132.6, CH | H-1, H-3 | C-4 |
| 3 | 7.33, dd (15.0, 11.0) | 154.4, CH | H-2, H-4 | C-1, C-5 |
| 4 | 6.67, ddd (15.2, 11.0, 1.8) | 129.5, CH | H-3, H-5 | C-3, C-6 |
| 5 | 6.47, dd (15.2, 5.2) | 147.6, CH | H-4, H-6 | C-3, C-6 |
| 6 | 4.66, dd (5.2, 2.0, 1.8) | 71.9, CH | H-5, H-7 | |
| 7 | 3.54, dd (8.8, 2.0) | 77.6, CH | H-6, H-8 | C-8 |
| 8 | 4.01, dd (8.8, 2.8,) | 64.6, CH | H-7, $H_2$-9 | |
| 9a | 2.10, ddd (14.3, 7.2, 2.8) | 27.9, $CH_2$ | H-8, $H_b$-9, $H_3$-10 | C-10 |
| 9b | 1.70, ddd (14.3, 7.2, 1.8) | 10.6, $CH_3$ | H-8, $H_a$-9, $H_3$-10 | C-8 |
| 10 | 1.06, d (7.2) | | H-8, $H_2$-9, $H_3$-10 | C-9 |
| 6-OH$^a$ | 5.21, d (6.2) | | H-6 | C-8 |
| 7-OH$^a$ | 5.11, d (7.7) | | H-7 | |

$^a$Observed in DMSO-$d_6$;
$^b$assigned from HSQC experiment

The following captures the analytical efforts involved in the structure elucidation of compound 4.

The HRMS analysis of 4 showed a distinctive isotopic cluster for $[M+Cl]^-$ at m/z 253.0404/255.0376 consistent with a molecular formula $C_{10}H_{15}ClO_3$ (calcd. 253.0398/255.0369). The $^1$H NMR spectrum of 4 indicated the existence of an aldehyde function δ 9.53 (1H, d, J=8.0 Hz), in addition to four signals characteristic of conjugated olefinic protons at δ6.15 (1H, dd, J=15.0 and 8.0 Hz), δ7.33 (1H, dd, J=15.0 and 11.0 Hz), δ6.67 (1H, ddd, J=15.2, 11.0 and 1.8 Hz) and δ6.47 (1H, dd, J=15.2 and 5.2 Hz). The latter were attributed to H-2, H-3, H-4 and H-5 of a linear system. The COSY experiment firmly established a single spin system from H-1 to H-10. In the absence of a direct carbon experiment due to insufficient sample, the carbon shifts were assigned with the aid of edited-HSQC and HMBC experiments (Table 1). The data revealed compound 4 to have an oxylipin structure. In addition to the aldehyde carbonyl ($\delta_C$ 196.4) and olefinic carbons ($\delta_C$ 132.6, 154.4, 129.5 and 147.6), three additional low-field resonances were assigned at $\delta_C$ 71.9 (C-6) and 77.6 (C-7) for two oxymethines, and at $\delta_C$ 64.6 (C-8) indicative of bearing a chlorine atom. The connectivity from C-1 to C-10 was further established by HMBC experiment. Two additional resonances at δ 5.21 (1H, d, J=6.2 Hz) and δ 5.11 (1H, d, J=7.7 Hz) in the $^1$H NMR spectrum acquired in DMSO-$d_6$ supported the presence of exchangeable protons that were assigned to the hydroxy groups at C-6 and C-7, respectively. Therefore the planar structure for 4 was determined as (2E,4E)-8-chloro-6,7-dihydroxy-deca-2,4-dienal:

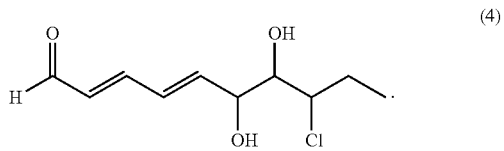

(2E,4E)-8-chloro-6,7-dihydroxydeca-2,4-dienal

Example 2: Cell Culture

All cells were maintained at 37° C. in humidified $CO_2$ atmosphere in respective media (IMR-32: EMEM; LNCaP:

RPMI 1640; RAW264.7: DMEM) supplemented with 10% heat-inactivated FBS from HyClone (Logan, Utah).

Example 3: ARE-Luc Reporter Assay in IMR-32 and LNCaP Cells

ARE luciferase reporter plasmid (50 ng/well) and CMV-GFP (10 ng/well) plasmid for monitoring transfection efficiency were co-transfected into IMR-32 cells ($3\times10^4$ cells/well) and LNCaP cells ($2\times10^4$ cells/well) using FUGENE HD (Roche) as transfection reagent following manufacturer's instructions. Transfected cells were seeded in 96-well plates and incubated for 24 h. Cells were treated with *Ulva* fractions, compounds, positive controls (tBHQ and sulforaphane at 10 µM) and solvent control (1% DMSO) in triplicate and allowed to incubate for an additional 24 h before luciferase activity was measured. Activity was detected using BriteLite (PerkinElmer) detection reagent for luminescence.

Example 4: Immunoblot Analysis and Results

IMR-32 cells ($6\times10^5$ cells/well) were plated in 6-well plates 24 h before treatment. Cells were transfected with compounds or vehicle, and incubated for 24 h. The whole-cell lysates were prepared by using PhosphoSafe lysis buffer (Novagen). Alternatively, nuclear and cytoplasmic proteins were separated by using the NE-PER reagent kit (Pierce). The protein concentrations of the samples were determined using the BCA method (Pierce), and cell lysates containing equal amounts of protein were separated by SDS-PAGE, transferred to PVDF membranes, probed with antibodies and detected with the Supersignal Femto Western blotting kit (Pierce). NQO1 and Nrf2 antibodies were obtained from Abcam (Cambridge, Mass.), β-actin, β-tubulin, secondary anti-rabbit and anti-mouse antibodies from Cell Signaling (Beverly, Mass.), and Oct1 antibody from Santa Cruz Biotechnology (Santa Cruz, Calif.).

Example 5: RNA Extraction and Quantitative PCR (qPCR) Analysis for Nrf2 and NQO1 Expression in IMR-32 Cells IMR-32 cells ($1\times10^6$ cells/well) were seeded in 6-well plates one day before treatment. Cells were treated with variable concentrations of purified compounds 1-4 for 12 h. Total RNA was extracted with the RNeasy Mini Kit (Qiagen). cDNA was synthesized from 2 µg of total RNA by using SuperScript II Reverse Transcriptase (Invitrogen) and Oligo(dT)$_{12-18}$ primer (Invitrogen). Real-time PCR was performed in triplicate using GAPDH expression as internal control for normalization.

Example 6: Inhibitor Studies

IMR-32 cells were seeded in 6-well dishes ($6\times10^5$ cells/well) one day before treatment. After pretreatment with the P13K inhibitor LY294002 (25 µM) or the MEK1 inhibitor PD98059 (50 µM) for 30 min, cells were treated with fractions NP3, NP4, NP5, and P4 for 24 h, and then proteins were harvested and subjected to immunoblot analysis.

Example 7: RNA Interference Experiments

Nontargeting control siRNA and siGENOME SMART pool siRNA reagents targeting NRF2 (mixture of 4 siRNAs) were obtained from Dharmacon. IMR-32 cells were seeded in 6-well dishes ($3\times10^5$ cells/well) 24 h prior to transfection. SiRNAs were transfected with siLentFect at the effective dose of 50 nM. 60 h after siRNA transfection, cells were treated with fractions NP3, NP4, NP5, and P4 or vehicle for 24 h before total protein lysates were collected and subjected to immunoblot analysis.

Example 8: Glutathione Assays

IMR-32 cells were seeded in 6-well dishes ($1.5\times10^6$ cells/well). 24 h later, the cells were treated with fractions or vehicle for 2, 8, 16, or 24 h. The treated cells were washed twice with PBS and centrifuged at 600 g for 6 min to obtain the cell pellet. The volume of the cell pellet was measured and resuspended in 3 volumes of 5% sulfosalicylic acid solution. The cell suspensions were frozen and thawed twice (using liquid nitrogen to freeze and a 37° C. water bath to thaw) and incubated for 5 min at 4° C., and centrifuged at 10,000 g for 10 min at 4° C. The supernatant was used as glutathione stock. The concentrations of total (reduced and oxidized) glutathione (GSH+GSSG) were assessed using Glutathione Assay Kit (Sigma), following the manufacturer's instructions as described [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013].

Example 9: In Vivo Studies

ARE-human placental alkaline phosphatase transgenic mice were bred and genotyped using 51 basepair segment of the rat Nqo1 promoter upstream of a heat-stable human placental alkaline phosphatase (hPAP) reporter gene construct as described [Chapman V J, Chapman D J. In Seaweeds and Their Uses. (Chapman and Hall, New York) pp 62-67; 1980]. The presence of the transgene was confirmed by PCR amplification of a portion of the inserted gene. ARE-hPAP negative littermates were used as background controls for endogenous alkaline phosphatase activity. The animals were housed at the University of Florida animal facility and treated in accordance with all IACUC regulations and maintained under standard laboratory conditions.

Male transgenic mice (~35 g; n=3) between 12-16 weeks of age were gavaged with a single dose (5 mg; ~140 mg/kg) of prioritized fractions NP3, NP4, NP5 and P4. Male control mice (n=3) from both transgenic and non-transgenic (for hPAP activity) sets were fed with 200 µL of the vehicle (10% DMSO; 10% Cremophor in PBS) and various tissues harvested 12 h post feeding. Total RNA for RT-PCR was isolated using Trizol reagent (Invitrogen) and protein for hPAP enzyme activity using freshly prepared TMNC buffer as described [Johnson D A, Andrews G K, Xu W, Johnson J A. Activation of the antioxidant response element in primary cortical neuronal cultures derived from transgenic reporter mice. *J. Neurochem.* 81:1233-1241; 2002].

Example 10: hPAP Enzyme Activity Assay

For alkaline phosphatase tissue activity, tissues were homogenized in TMNC (0.05 M Tris, 0.005 M $MgCl_2$, 0.1 M NaCl, 1% [CHAPS]) lysis buffer and refrozen at −80° C. Total protein was quantified using BCA assay kit (Pierce) for normalization. Endogenous phosphatase activity was heat inactivated at 65° C. for 30 min then incubated at room temperature in the presence of a chemiluminescent CSPD substrate (Tropix) for alkaline phosphatase. Activity was assessed by measuring the resulting luminescent signal representing relative hPAP activity according to manufacturer's instruction for Phospho-Light Reporter Gene Assay System (Applied Biosystems).

Example 11: Assay for Induction of iNOS and Cox2 in Macrophage Cells

RAW264.7 cells were seeded in 6-wells for RNA experiments and treated with different concentrations of *Ulva* fractions for 1 h. Cells were treated with 1 µg/mL of LPS or 10 ng/mL of IFN-γ and incubated for 12 h. Total RNA was extracted using RNeasy Mini Kit. PCR analyses were performed on the aliquots of the cDNA preparations to detect iNOS, Cox2, Nqo1 and β-actin (internal standard) expression.

Example 12: NO Assay

RAW 264.7 cells were seeded in 96 wells ($2\times10^4$ cells/well) and were pretreated for 1 h with different concentrations of *Ulva* fractions or solvent control (1% EtOH), prior to adding LPS (1 µg/mL) or IFN-γ (10 ng/mL). NO production in culture supernatant was assessed after 24 h by measuring nitrite concentration, an oxidative product of NO. Nitrite production in LPS and IFN-γ stimulated RAW264.7 cells was measured by mixing 50 µL of culture supernatant with 50 µL of Griess reagent (Promega, Madison, Wis.), and absorbance was measured at 540 nm against a calibration curve generated for fresh sodium nitrite standard. All assays were performed in triplicate and data reported as normalized values.

Example 13: $PGE_2$ Assay

RAW264.7 cells were seeded in 96-well plate ($4\times10^4$ cells/well) 24 h prior to treatment. Fractions or vehicle were pretreated for 1 h before adding LPS (1 µg/mL), and incubated for further 24 h. The supernatant was transferred to fresh collection tubes and used for the assay. Amersham Prostaglandin $E_2$ Biotrak Enzyme immunoassay (EIA) system (GE Healthcare) was used for the assay and the instructions were followed. 50 µL of sample were added to diluted assay buffer in a 96-well plate, followed by 50 µL of diluted $PGE_2$ antibody and 50 µL of diluted $PGE_2$ conjugate. After 1 h incubation at room temperature, the wells were washed four times with wash buffer. 150 µL of room temperature equilibrated enzyme substrate was pipetted into each well immediately after wash. After 30 min incubation on a shaker, 100 µL of 1 M sulfuric acid were added to halt the reaction. The signals were read at 450 nm using SpectraMax M5 plate reader.

Example 14: Nqo1 Activity Assay

Wild-type ($8\times10^3$ cells/well), $Nrf2^{-/-}$ ($8\times10^3$ cells/well) and $Keap1^{-/-}$ ($4\times10^3$ cells/well) fibroblasts were plated in 96-well plates, and 24 h later the cells were incubated with various concentrations of compound or solvent control for 40 h. The activity was measured as described [Prochaska H J, Santamaria A B. Direct measurement of NAD(P)H:quinone reductase from cells cultured in microtiter wells: a screening assay for anticarcinogenic enzyme inducers. *Anal Biochem* 1988; 169:328-336].

Biological Results

We previously sampled a variety of field-collected seaweeds from the Florida coastline and, using an ARE-luciferase reporter gene assay, found that *Ulva lactuca* is a particularly potent activator of the ARE. These *U. lactuca* field collections yielded monounsaturated fatty acid type compounds as representative ARE-active components [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013]. Large-scale cultivation of *Ulva* sp. now enabled us to rigorously evaluate the biological activity of the resulting extracts after carrying out a bioassay-guided fractionation. We used two cell lines for our initial assessment of ARE activity: (1) IMR-32 human neuroblastoma cells, a commonly used cellular model of oxidative stress which we have previously used to identify ARE activators, and (2) androgen-sensitive (LNCaP) prostate cancer cells, since a common genetic feature of prostate cancer is the silencing of a GST gene (ARE-regulated) [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013; Lee W H, Morton R A, Epstein J I, Brooks J D, Campbell P A, Bova G S, et al. Cytidine methylation of regulatory sequences near the π-class glutathione S-transferase gene accompanies human prostatic carcinogenesis. *Proc. Natl. Acad. Sci. USA* 91:11733-11737; 1994; Lee W-H, Isaacs W B, Bova G S, Nelson W G. CG island methylation changes near the GSTP1 gene in prostatic carcinoma cells detected using the polymerase chain reaction: a new prostatic biomarker. *Cancer Epidemiol. Biomark. Prev.* 6:443-450; 1997; Lin X, Tascilar M, Lee W H, Vies W J, Lee B H, Veeraswamy R, et al. GSTP1 cpG island hypermethylation is responsible for the absence of GSTP1 expression in human prostate cancer cells. *Am. J. Pathol.* 159:1815-1826; 2001; Wang R, Kern J T, Goodfriend T L, Ball D L, Luesch H. Activation of the antioxidant response element by specific oxidized metabolites of linoleic acid. *Prostaglandins Leukotrienes Essent. Fatty Acids* 81:53-59; 2009; Hur W, Sun Z, Jiang T, Mason D E, Peters E C, Zhang D D, et al. A small-molecule inducer of the antioxidant response element. *Chem. Biol.* 17:537-547; 2010; Liu Y, Kern J T, Walker J R, Johnson J A, Schultz P G, Luesch H. A genomic screen for activators of the antioxidant response element. *Proc. Natl. Acad. Sci. USA* 104:5205-5210; 2007]. Prostate cancer may be prevented most suitably by compounds acting through an antioxidant-type mechanism; however, the cancer preventive agent sulforaphane shows diminished responsiveness in androgen-insensitive cell lines [Brooks J D, Paton V G, Vidanes G. Potent induction of phase 2 enzymes in human prostate cells by sulforaphane. *Cancer Epidemiol. Biomark. Prev.* 10:949-954; 2001].

The freeze-dried sample was successively extracted with EtOAc and EtOH, followed by silica gel or C18 reversed-phase chromatography, respectively (FIG. 1A), to yield several activity-enriched fractions, suggesting the presence of multiple bioactive components. Further chemical profiling and purification indeed confirmed that the ARE activity is attributed to an array of metabolites, prompting us to initially characterize the biological activities of the chromatography fractions rather than individual components and to also capture potential synergistic effects. The EtOAc (nonpolar, NP) extract yielded the most active fractions, designated NP3, NP4 and NP5 (FIG. 1A), in the reporter assay (FIG. 1B). NP3 and NP4 activated the reporter 25- and 11-fold, respectively, at 32 µg/mL and showed toxicity at higher concentrations (100 μg/mL) in the IMR-32 cells. NP5 and the EtOH (polar, P) extract-derived P4 fraction (FIG. 1A) were highly active at 100 μg/mL, with 23- and 36-fold activity, respectively (FIG. 1B). These activities correlated with the effects observed on the transcription of endogenous NQO1, an ARE-regulated target gene, as determined by quantitative PCR (qPCR) after reverse transcription (RT). The four active fractions induced NQO1 expression up to 8- to 18-fold (FIG. 1C). Transcript levels of NRF2 were at most marginally increased in NP4, NP5 and P4 (1.8- to 2.5-fold) and to a slightly greater extent in fraction NP3 (4.2-fold) (FIG. 1D). Overall these data suggest that Nrf2 transcription factor activation on the protein level rather than gene expression level must have been largely responsible for the potent NQO1 induction. The reporter activation and induction of NQO1 transcription were not cell-type specific, as similar results were obtained in LNCaP cells (FIG. 1E-G). In both cell lines the magnitudes of activation rivaled those of the corresponding positive controls tert-butylhydroquinone (tBHQ) and sulforaphane (SF) (FIG. 1B-G).

Figure 9C:
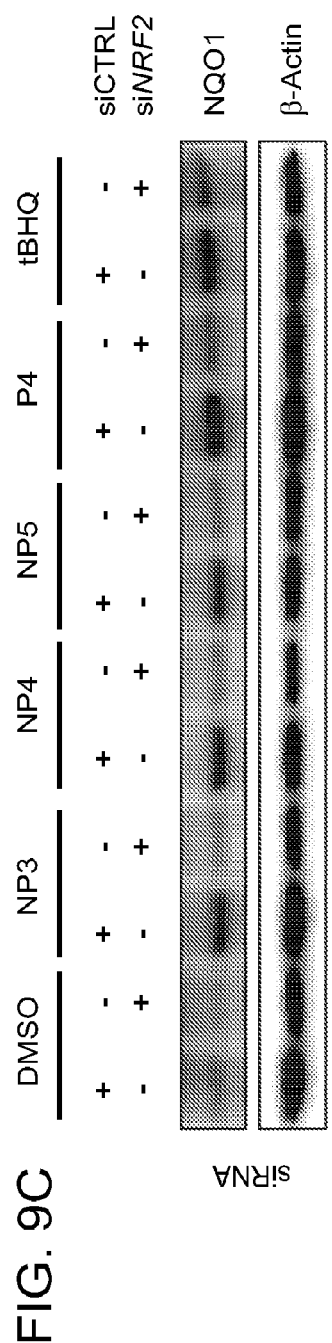
FIG. 9. depicts the downstream responses and mechanism of ARE-controlled gene expression of active fractions in IMR-32 cells.
Figure 9D:
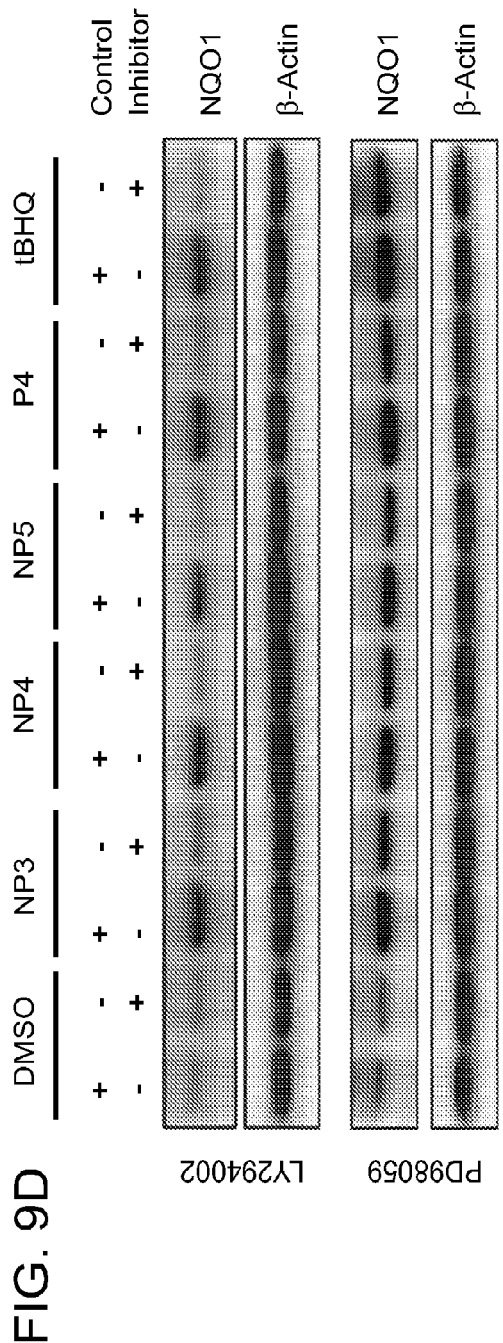
Figure 9E:
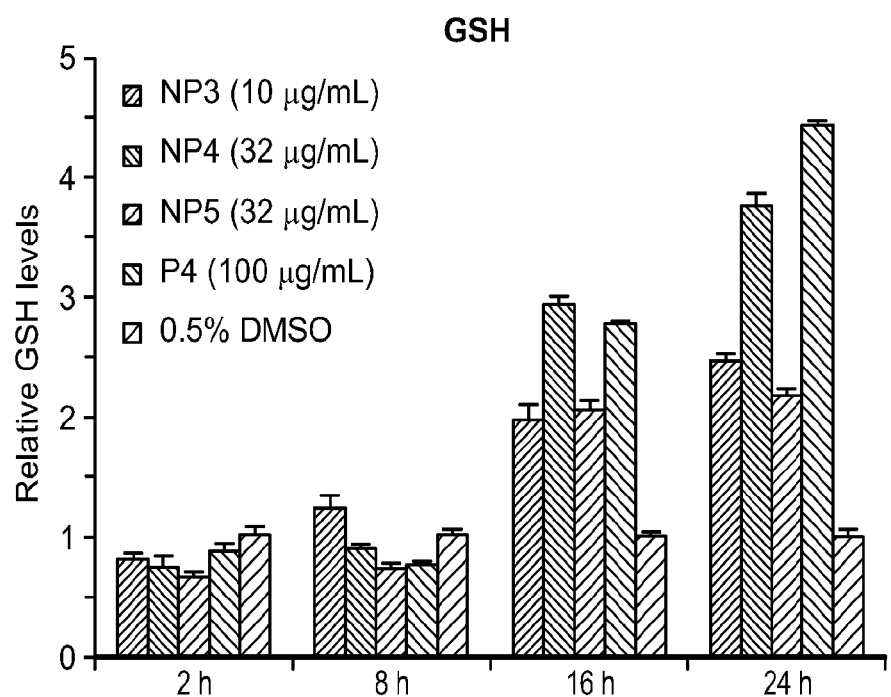

Next, we tested whether NQO1 protein levels paralleled the increased transcript levels. We chose the IMR-32 cell line, which gave a more robust induction of NQO1 transcription. Again, all four fractions strongly elevated NQO1 protein levels as measured by immunoblot analysis, and the optimal concentrations were sample-dependent (FIG. 9A). We found that nuclear extracts derived from all treated cells were highly enriched in Nrf2 (FIG. 9B), suggesting that the fractions caused Nrf2 nuclear translocation. To determine if the increase in NQO1 protein relied on Nrf2, we depleted cells of Nrf2 via RNA interference using previously validated NRF2-specific siRNAs and then treated with fractions at the active concentrations [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013; Liu Y, Kern J T, Walker J R, Johnson J A, Schultz P G, Luesch H. A genomic screen for activators of the antioxidant response element. *Proc. Natl. Acad. Sci. USA* 104:5205-5210; 2007]. Expectedly, we found that none of the *Ulva* fractions was able to promote NQO1 levels in siNRF2-treated IMR-32 cells (FIG. 9C), indicating that Nrf2 is the essential transcription factor mediating NQO1 induction by the *Ulva* fractions. Furthermore, pre-treatment with a PI3K inhibitor prevented NQO1 induction, while a MEK1 inhibitor had only marginal effects (FIG. 9D), indicating that the activity of the fractions in this cell type relies on a functional PI3K signaling pathway, but only to a much lesser extent on MAPK signaling, as observed for field-collected *U. lactuca* [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013]. We then tested the effects of the fractions at their non-toxic active concentration on levels of the major small-molecule antioxidant, glutathione, in a time-dependent manner. We observed a 10-30% drop of glutathione levels after 2 h (FIG. 9E), possibly due to transient disruption of the cellular redox status. Upon longer incubation times (16 and 24 h) we measured a strong increase of glutathione levels of up to 220-440%, depending on the fraction, consistent with ARE activation since glutathione biosynthetic genes are regulated by the Nrf2-ARE pathway [Wang R, Paul V J, Luesch H. Seaweed extracts and unsaturated fatty acid constituents from the green alga *Ulva lactuca* as activators of the cytoprotective Nrf2-ARE pathway. *Free Rad. Biol. Med.* doi10.1016/j.freeradbiomed.2012.12.019 (Epub Jan. 4, 2013); 2013].

To test if the in vitro ARE activity translates into in vivo activity, and thereby if the mixtures are sufficiently bioavailable and/or have a low enough clearance rate and, by extrapolation, if *Ulva* sp. consumption can lead to activation of the endogenous ARE-regulated defense system, we treated mice with the bioactive fractions by oral gavage. We used transgenic mice developed by Johnson, in which the ARE sequence of the rat Nqo1 enhancer region has been linked to human placental alkaline phosphatase (hPAP) reporter gene, a model that is suitable to evaluate enzymatic and immunohistochemical responses [Johnson D A, Andrews G K, Xu W, Johnson J A. Activation of the antioxidant response element in primary cortical neuronal cultures derived from transgenic reporter mice. *J. Neurochem.* 81:1233-1241; 2002]. These mice were previously used to test the effectiveness of triterpenoids as inducers of the Nrf2-ARE pathway in vivo [Yates M S, Tauchi M, Katsuoka F, Flanders K C, Liby K T, Honda T, et al. Pharmacodynamic characterization of chemopreventive triterpenoids as exceptionally potent inducers of Nrf2-regulated genes. *Mol. Cancer Ther.* 6:154-162; 2007]. Analogously, we fed prioritized fractions to male mice (single dose of 140 mg/kg, n=3), harvested tissues 12 h later and, to assess hPAP activity, focused on two tissues with (1) detoxification responsibilities (liver) and (2) potentially high degree of oxidative activity (lung). In both cases we observed increased activity by the treatments, up to 3.2-fold in liver and up to 3.9-fold in lung (FIG. 10A), suggesting that the active *Ulva* components are sufficiently bioavailable based on the measured functional response.

These encouraging results from the reporter assay prompted us to analyze in detail the endogenous Nqo1 expression by RT-qPCR relative to controls, as a measure of the true antioxidant enzyme status potential in the tissues. We also extended the analysis to additional tissues. All of the prioritized fractions derived from cultured *Ulva* showed in vivo activity, but the upregulation of Nqo1 spiked in different tissues, as roughly represented in a heat map for averages of all mice for active fractions (FIG. 10B). Different fractions preferentially induced Nqo1 in different tissues, suggesting that certain organs can be targeted with distinct fractions to achieve a protective effect. This is likely due to different chemistry and bioavailability of different components, which remains to be investigated.

Compounds 1-4 were investigated for ARE activity by evaluating the activation of NQO1 transcription in IMR-32 cells in a dose dependent manner (FIG. 11B). Compound 4 showed the most pronounced activity among the purified metabolites (6.4-fold at 20 μg/mL) comparable to tBHQ (5.9-fold) under identical conditions. At the same time, all purified compounds had no or only marginal effects on NRF2 transcript levels.

Figure 12E:
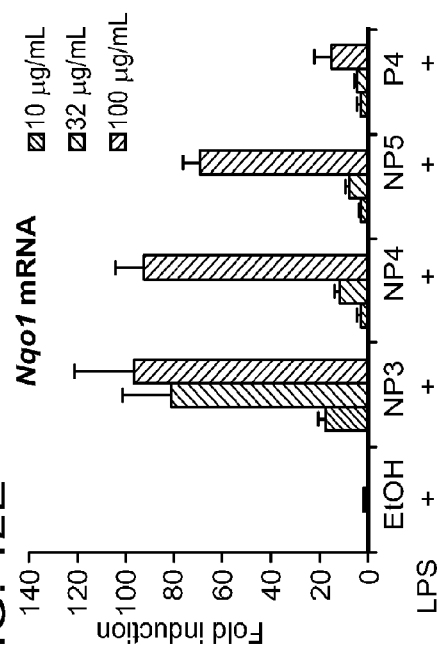
FIG. 12. depicts the effects of prioritized fractions on pro-inflammatory gene expression and mediators in macrophage RAW 264.7 cells and mouse embryonic fibroblasts (MEFs).
Figure 12F:
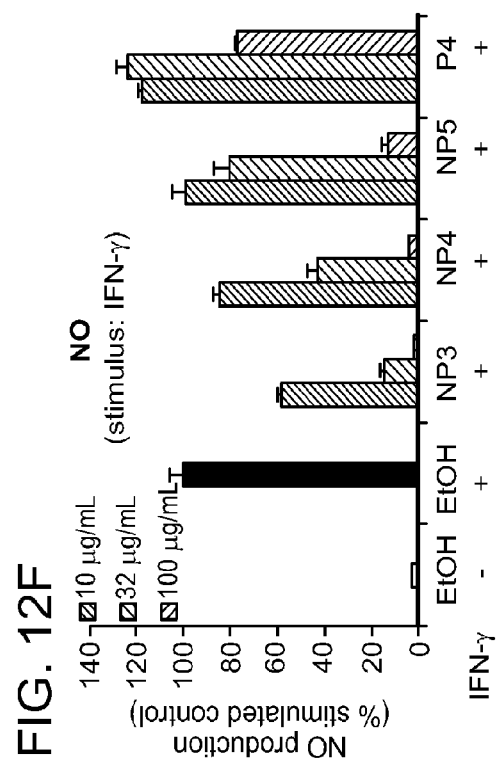
Figure 12C:
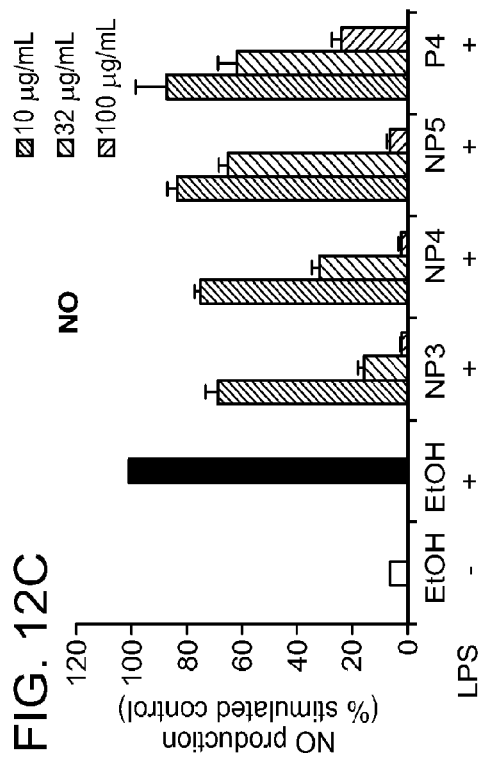
Figure 12D:
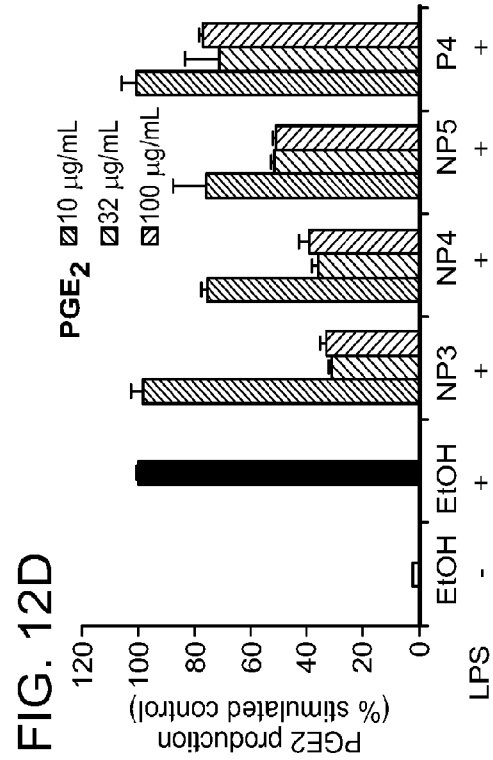

We then decided to measure downstream physiological effects as a result of phase II and antioxidant enzyme upregulation in a disease-relevant context. Since there is evidence that links the induction of phase II enzymes with protection from inflammatory stress, we used the RAW 264.7 macrophage cell line to correlate ARE activation to LPS- and IFN-γ stimulated iNOS and Cox2 transcription [Chen X-L, Kunsch C. Induction of cytoprotective genes through Nrf2/antioxidant response element pathway: a new therapeutic approach for the treatment of inflammatory diseases. Curr Pharm Des 2004; 10:879-891; Dinkova-Kostova, A T, Liby K T, Stephenson K K, Holtzclaw W D, Gao X, Suh N, et al. Extremely potent triterpenoid inducers of the phase 2 response: Correlations of protection against oxidant and inflammatory stress. *Proc. Natl. Acad. Sci. USA* 102:4584-4589; 2005]. All fractions (NP3, NP4, NP5, P4) were able to abrogate LPS-induced expression of iNOS and Cox2, two pro-inflammatory target genes, almost completely at higher concentrations (iNOS, FIG. 11A) or partially (Cox2) (FIG. 12B). We then measured the products of iNOS and Cox2 enzyme action, i.e., nitric oxide (NO) and prostaglandin E2 ($PGE_2$), respectively. All fractions (NP3, NP4, NP5, P4) strongly reduced NO production in a dose-dependent manner (FIG. 12C). Similarly, using ELISA we determined that these fractions also partially decreased $PGE_2$ levels (FIG. 12D), paralleling the RT-qPCR results. The knockdown was inversely correlated with Nqo1 transcript levels, which were strongly elevated in RAW264.7 cells in a dose-dependent manner (FIG. 12E), suggesting that ARE activation is a relevant mechanism by which the *Ulva* fractions exert their anti-inflammatory effect. Furthermore, NP3 appeared to be most potent in both the knockdown of iNOS and Cox2 and the induction of Nqo1 mRNA levels, consistent with the data obtained in IMR-32 and LNCaP cells. To determine if the anti-inflammatory activity is stimulus-dependent, we found that three of the fractions (NP3, NP4, NP5) also inhibited IFN-γ induced NO production, while the weakest ARE activator, P4, did not have a substantial effect (FIG. 12F). In summary, these data suggest that the anti-inflammatory effect of *Ulva* fractions is largely stimulus-independent, yet that there are some notable differences that may be attributed to the different chemical composition of the fractions.

Figure 12G:
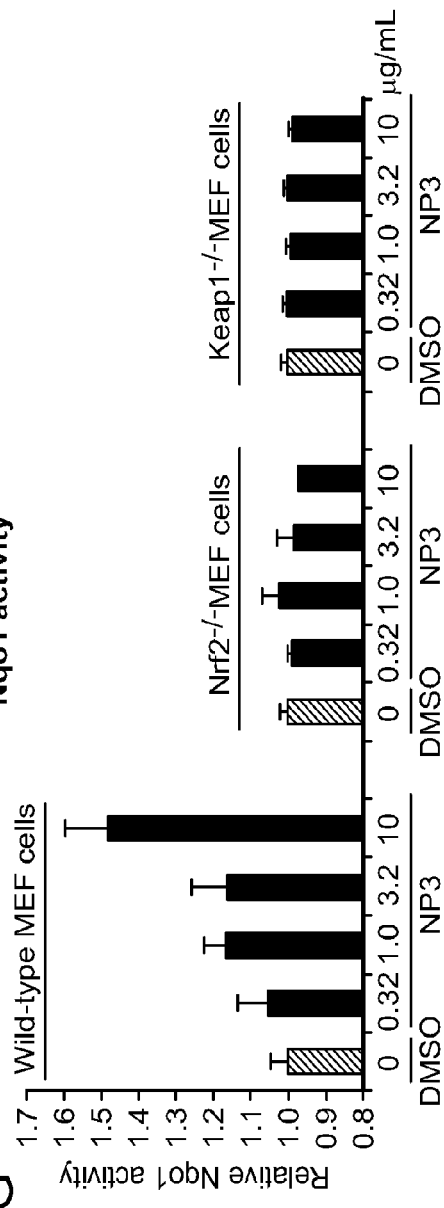
Figure 12H:
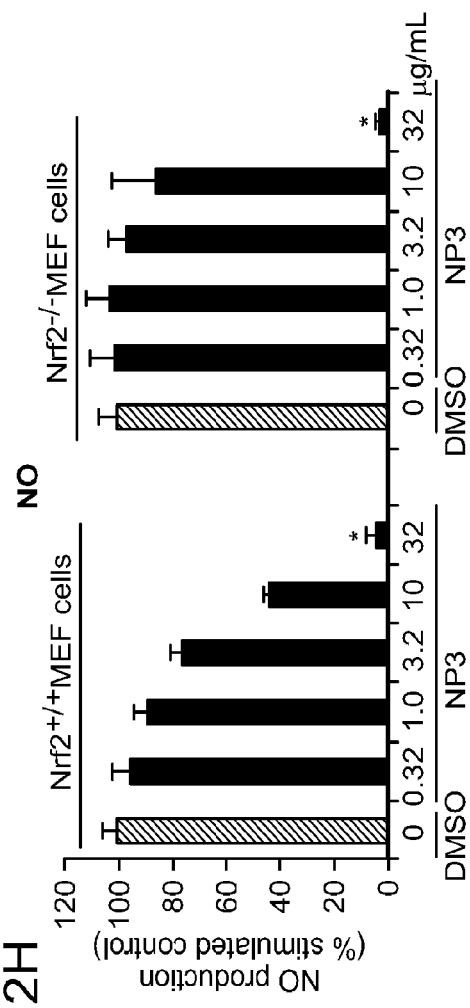

The most potent and chemically most characterized fraction (NP3) was then used to test for Nqo1 activity and NO synthesis inhibition in isogenic mouse embryonic fibroblast (MEF) cells as previously described [Dinkova-Kostova A T, Liby K T, Stephenson K K, Holtzclaw W D, Gao X, Suh N, et al. Extremely potent triterpenoid inducers of the phase 2 response: Correlations of protection against oxidant and inflammatory stress. Proc Natl Acad Sci USA 2005; 102: 4584-4589]. Fraction NP3 induced Nqo1 activity only in wild-type MEFs but not in Nrf2 knockout ($Nrf2^{-/-}$) and Keap1-knockout ($Keap1^{-/-}$) cells (FIG. 12G). When MEFs were stimulated with IFN-γ and TNF-α, fraction NP3 reduced NO levels only in wild-type MEFs but not $Nrf2^{-/-}$ MEFs up to 10 μg/mL (FIG. 12H). The possibility of non-Nrf2 mediated anti-inflammatory effects at higher concentration as previously observed for other ARE activators cannot be excluded, since the apparent reduction of NO in $Nrf2^{-/-}$ MEFs at 32 μg/mL overlapped with the toxicity [Liu H, Dinkova-Kostova A T, Talalay P. Coordinate regulation of enzyme markers for inflammation and for protection against oxidants and electrophiles. Proc Natl Acad Sci USA 2008; 105:15926-15931]. In summary, the anti-inflammatory effects of the investigated *Ulva* fraction appear to be mediated by an Nrf2/ARE-dependent mechanism.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A method of treating a human suffering from prostate cancer comprising administering to said human suffering from prostate cancer a therapeutically effective amount of an extract of cultivated seaweed *Ulva* sp., wherein said human is effectively treated after having the cultivated seaweed *Ulva* sp. administered to him/her and wherein said extract is extracted with a solvent selected from the group consisting of ethyl acetate, hexane, isopropanol, acetonitrile and dichloromethane.

* * * * *